US011369484B2

(12) United States Patent
Wagner et al.

(10) Patent No.: US 11,369,484 B2
(45) Date of Patent: Jun. 28, 2022

(54) EXPANDABLE FUSION DEVICE FOR POSITIONING BETWEEN ADJACENT VERTEBRAL BODIES

(71) Applicant: Flexuspine, Inc., Tyler, TX (US)

(72) Inventors: Erik Wagner, Austin, TX (US); Michael Schular, Pittsburgh, PA (US)

(73) Assignee: Flexuspine Inc., Tyler, TX (US)

( * ) Notice: Subject to any disclaimer, the term of this patent is extended or adjusted under 35 U.S.C. 154(b) by 0 days.

(21) Appl. No.: 16/192,932

(22) Filed: Nov. 16, 2018

(65) Prior Publication Data
US 2019/0321190 A1   Oct. 24, 2019

Related U.S. Application Data

(63) Continuation of application No. 15/351,943, filed on Nov. 15, 2016, now abandoned, which is a
(Continued)

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/4455* (2013.01); *A61F 2/4611* (2013.01); *A61F 2/4465* (2013.01);
(Continued)

(58) Field of Classification Search
None
See application file for complete search history.

(56) References Cited

U.S. PATENT DOCUMENTS 3,848,601 A    11/1974  Ma et al.
3,867,728 A    2/1975   Substad et al.
(Continued)

FOREIGN PATENT DOCUMENTS

EP    1090595    11/2001
FR    2716616    9/1995
(Continued)

OTHER PUBLICATIONS

Case IPR2015-01721: EX1005: Declaration of Jorge A. Ochoa, P.E.
(Continued)

*Primary Examiner* — Tessa M Matthews
(74) *Attorney, Agent, or Firm* — Kim IP Law Group LLC

(57) ABSTRACT

In some embodiments, system and/or method may include an intervertebral implant for a human spine including an upper body, a lower body, first and second expansion members, and an expansion mechanism. A superior surface of the upper body may function to engage a first vertebra of the human spine. An inferior surface of the lower body may function to engage a second vertebra of the human spine. The first expansion member may include at least a first angled portion positionable, during use, between the upper body and the lower body. The second expansion member may include at least a second angled portion positionable, during use, between the upper body and the lower body. An expansion mechanism may convey, during use, the first and second angled portions in opposing directions increasing a separation distance between the upper body and the lower body.

21 Claims, 21 Drawing Sheets

Related U.S. Application Data continuation of application No. 14/185,561, filed on Feb. 20, 2014, now Pat. No. 9,492,288.

(60) Provisional application No. 61/766,982, filed on Feb. 20, 2013.

(51) Int. Cl.
*A61F 2/28* (2006.01)
*A61F 2/30* (2006.01)

(52) U.S. Cl.
CPC ............. *A61F 2002/2835* (2013.01); *A61F 2002/30507* (2013.01); *A61F 2002/30556* (2013.01); *A61F 2002/30772* (2013.01); *A61F 2002/30904* (2013.01); *A61F 2002/4627* (2013.01)

(56) References Cited

U.S. PATENT DOCUMENTS

| | | |
|---|---|---|
| 4,309,777 A | 1/1982 | Patil |
| 4,349,921 A | 9/1982 | Kuntz |
| 4,611,581 A | 9/1986 | Steffee |
| 4,657,550 A | 4/1987 | Daher |
| 4,696,290 A | 9/1987 | Steffee |
| 4,743,260 A | 5/1988 | Burton |
| 4,759,766 A | 7/1988 | Buettner-Janz et al. |
| 4,759,769 A | 7/1988 | Hedman et al. |
| 4,763,644 A | 8/1988 | Webb |
| 4,772,287 A | 9/1988 | Ray et al. |
| 4,854,311 A | 8/1989 | Steffee |
| 4,863,476 A | 9/1989 | Shepperd |
| 4,863,477 A | 9/1989 | Monson |
| 4,907,577 A | 3/1990 | Wu |
| 4,911,718 A | 3/1990 | Lee et al. |
| 4,932,975 A | 6/1990 | Main et al. |
| 4,946,378 A | 8/1990 | Hirayama et al. |
| 4,946,458 A | 8/1990 | Harms et al. |
| 5,042,982 A | 8/1991 | Harms et al. |
| 5,047,055 A | 9/1991 | Bao et al. |
| 5,059,194 A | 10/1991 | Michelson |
| 5,071,437 A | 12/1991 | Steffee |
| 5,092,867 A | 3/1992 | Harms et al. |
| 5,108,438 A | 4/1992 | Stone |
| 5,123,926 A | 6/1992 | Pisharodi |
| 5,171,278 A | 12/1992 | Pisharodi |
| 5,171,281 A | 12/1992 | Parsons et al. |
| 5,180,393 A | 1/1993 | Commarmond |
| 5,192,326 A | 3/1993 | Bao et al. |
| 5,196,013 A | 3/1993 | Harms et al. |
| 5,207,678 A | 5/1993 | Harms et al. |
| 5,217,497 A | 6/1993 | Mehdian |
| 5,246,458 A | 9/1993 | Graham |
| 5,258,031 A | 11/1993 | Salib et al. |
| 5,261,909 A | 11/1993 | Sutterlin et al. |
| 5,306,307 A | 4/1994 | Senter et al. |
| 5,306,309 A | 4/1994 | Wagner et al. |
| 5,314,477 A | 5/1994 | Marnay |
| 5,320,644 A | 6/1994 | Baumgartner |
| 5,336,223 A | 8/1994 | Rogers |
| 5,370,697 A | 12/1994 | Baumgartner |
| 5,375,823 A | 12/1994 | Navas |
| 5,397,364 A | 3/1995 | Kozak et al. |
| 5,401,269 A | 3/1995 | Buettner-Janz et al. |
| 5,403,315 A | 4/1995 | Ashman |
| 5,415,661 A | 5/1995 | Holmes |
| 5,458,643 A | 5/1995 | Heggeness et al. |
| 5,423,816 A | 6/1995 | Lin |
| 5,425,773 A | 6/1995 | Boyd et al. |
| 5,443,467 A | 8/1995 | Biedermann et al. |
| 5,458,642 A | 10/1995 | Beer et al. |
| 5,480,401 A | 1/1996 | Navas |
| 5,496,321 A | 3/1996 | Puno et al. |
| 5,498,263 A | 3/1996 | DiNello et al. |
| 5,507,816 A | 4/1996 | Bullivant |
| 5,514,132 A | 5/1996 | Csernatony et al. |
| 5,514,180 A | 5/1996 | Heggeness et al. |
| 5,522,899 A | 6/1996 | Michelson |
| 5,527,314 A | 6/1996 | Brumfield et al. |
| 5,534,028 A | 7/1996 | Bao et al. |
| 5,534,029 A | 7/1996 | Shima |
| 5,534,030 A | 7/1996 | Navarro et al. |
| 5,540,688 A | 7/1996 | Navas |
| 5,545,165 A | 8/1996 | Biedermann et al. |
| 5,556,431 A | 9/1996 | Buettner-Janz |
| 5,562,663 A | 10/1996 | Wisnewski et al. |
| 5,562,737 A | 10/1996 | Graf |
| 5,562,738 A | 10/1996 | Boyd et al. |
| 5,571,109 A | 11/1996 | Bertagnoli |
| 5,609,635 A | 3/1997 | Michelson |
| 5,624,442 A | 4/1997 | Mellinger et al. |
| 5,645,599 A | 7/1997 | Samani |
| 5,653,763 A | 8/1997 | Errico et al. |
| 5,665,122 A | 9/1997 | Kambin |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,701 A | 10/1997 | Yuan et al. |
| 5,676,702 A | 10/1997 | Ratron |
| 5,683,391 A | 11/1997 | Boyd |
| 5,683,464 A | 11/1997 | Wagner et al. |
| 5,683,465 A | 11/1997 | Shinn et al. |
| 5,702,450 A | 12/1997 | Bisserie |
| 5,725,527 A | 3/1998 | Biedermann et al. |
| 5,733,284 A | 3/1998 | Martin |
| 5,741,253 A | 4/1998 | Michelson |
| 5,755,797 A | 5/1998 | Baumgartner |
| 5,772,661 A | 6/1998 | Michelson |
| 5,776,199 A | 7/1998 | Michelson |
| 5,782,832 A | 7/1998 | Larsen et al. |
| 5,785,647 A | 7/1998 | Tompkins et al. |
| 5,797,909 A | 8/1998 | Michelson |
| 5,800,549 A | 9/1998 | Bao et al. |
| 5,800,550 A | 9/1998 | Sertich |
| 5,810,819 A | 9/1998 | Errico et al. |
| 5,824,093 A | 10/1998 | Ray et al. |
| 5,824,094 A | 10/1998 | Serhan et al. |
| 5,827,328 A | 10/1998 | Buttermann |
| 5,860,973 A | 1/1999 | Michelson |
| 5,861,041 A | 1/1999 | Tienboon |
| 5,863,293 A | 1/1999 | Richelsoph |
| 5,863,465 A | 1/1999 | Kinlen |
| 5,865,846 A | 2/1999 | Bryan et al. |
| 5,865,848 A | 2/1999 | Baker |
| 5,888,220 A | 3/1999 | Felt et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,928,243 A | 7/1999 | Guyer |
| 5,935,133 A | 8/1999 | Wagner et al. |
| 5,938,663 A | 8/1999 | Petreto |
| 5,951,555 A | 9/1999 | Rehak et al. |
| 5,961,518 A | 10/1999 | Errico et al. |
| 5,961,554 A | 10/1999 | Janson et al. |
| 5,964,769 A | 10/1999 | Wagner et al. |
| 5,976,186 A | 11/1999 | Bao et al. |
| 5,980,522 A | 11/1999 | Koros et al. |
| 5,984,967 A | 11/1999 | Zdeblick et al. |
| 5,989,250 A | 11/1999 | Wagner et al. |
| 5,989,290 A | 11/1999 | Biedermann et al. |
| 5,997,539 A | 12/1999 | Errico et al. |
| 6,001,130 A | 12/1999 | Bryan et al. |
| 6,017,344 A | 1/2000 | Errico et al. |
| 6,019,792 A | 2/2000 | Cauthen |
| 6,022,376 A | 2/2000 | Assell et al. |
| 6,030,389 A | 2/2000 | Wagner et al. |
| 6,039,763 A | 3/2000 | Shelokov |
| 6,045,552 A | 4/2000 | Zucherman et al. |
| 6,045,579 A | 4/2000 | Hochschuler et al. |
| 6,053,921 A | 4/2000 | Wagner et al. |

(56) References Cited

U.S. PATENT DOCUMENTS

| | | |
|---|---|---|
| 6,063,089 A | 5/2000 | Errico et al. |
| RE36,758 E | 6/2000 | Fitz |
| 6,080,193 A | 6/2000 | Hochschuler et al. |
| 6,093,205 A | 7/2000 | Mcleod et al. |
| 6,096,038 A | 8/2000 | Michelson |
| 6,099,531 A | 8/2000 | Bonutti |
| 6,102,950 A | 8/2000 | Vaccaro |
| 6,106,526 A | 8/2000 | Harms et al. |
| 6,110,210 A | 8/2000 | Norton et al. |
| 6,113,637 A | 9/2000 | Gill et al. |
| 6,123,707 A | 9/2000 | Wagner et al. |
| 6,126,689 A | 10/2000 | Brett |
| 6,132,430 A | 10/2000 | Wagner et al. |
| 6,132,464 A | 10/2000 | Martin |
| 6,132,465 A | 10/2000 | Ray et al. |
| 6,136,001 A | 10/2000 | Michelson |
| 6,136,031 A | 10/2000 | Middleton |
| 6,139,579 A | 10/2000 | Steffee et al. |
| 6,146,421 A | 11/2000 | Gordon et al. |
| 6,146,422 A | 11/2000 | Lawson |
| 6,156,067 A | 12/2000 | Bryan et al. |
| 6,159,244 A | 12/2000 | Suddaby |
| 6,162,252 A | 12/2000 | Kuras et al. |
| 6,165,218 A | 12/2000 | Husson et al. |
| 6,179,874 B1 | 1/2001 | Cauthen |
| 6,187,048 B1 | 2/2001 | Milner et al. |
| 6,200,348 B1 | 3/2001 | Biedermann et al. |
| 6,206,924 B1 | 3/2001 | Timm |
| 6,214,049 B1 | 4/2001 | Gayer et al. |
| 6,214,050 B1 | 4/2001 | Huene |
| 6,217,579 B1 | 4/2001 | Koros |
| 6,228,118 B1 | 5/2001 | Gordon |
| 6,231,609 B1 | 5/2001 | Mehdizadeh |
| 6,176,882 B1 | 6/2001 | Biedermann et al. |
| 6,241,730 B1 | 6/2001 | Alby |
| 6,264,656 B1 | 7/2001 | Michelson |
| 6,290,724 B1 | 9/2001 | Marino |
| 6,296,664 B1 | 10/2001 | Middleton |
| 6,315,797 B1 | 11/2001 | Middleton |
| 6,331,179 B1 | 12/2001 | Freid et al. |
| 6,348,071 B1 | 2/2002 | Steffee et al. |
| RE37,665 E | 4/2002 | Ralph et al. |
| 6,368,350 B1 | 4/2002 | Erickson |
| 6,368,351 B1 | 4/2002 | Glenn et al. |
| 6,371,990 B1 | 4/2002 | Ferree |
| 6,375,682 B1 | 4/2002 | Fleischmann et al. |
| 6,375,683 B1 | 4/2002 | Crozet et al. |
| 6,391,030 B1 | 5/2002 | Wagner et al. |
| 6,395,032 B1 | 5/2002 | Gauchet |
| 6,395,034 B1 | 5/2002 | Suddaby |
| 6,402,784 B1 | 6/2002 | Wardlaw |
| 6,402,785 B1 | 6/2002 | Zdeblick et al. |
| 6,409,766 B1 | 6/2002 | Brett |
| 6,413,259 B1 | 7/2002 | Lyons et al. |
| 6,416,515 B1 | 7/2002 | Wagner et al. |
| 6,419,703 B1 | 7/2002 | Fallin et al. |
| 6,419,704 B1 | 7/2002 | Ferree |
| 6,436,140 B1 | 8/2002 | Liu et al. |
| 6,440,168 B1 | 8/2002 | Cauthen |
| 6,442,814 B1 | 9/2002 | Landry et al. |
| 6,443,990 B1 | 9/2002 | Aebi et al. |
| 6,447,512 B1 | 9/2002 | Landry et al. |
| 6,447,544 B1 | 9/2002 | Michelson |
| 6,447,545 B1 | 9/2002 | Bagby |
| 6,451,021 B1 | 9/2002 | Ralph et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,475,218 B2 | 11/2002 | Gournay et al. |
| 6,478,822 B1 | 11/2002 | Leroux et al. |
| 6,478,823 B1 | 11/2002 | Michelson |
| 6,482,207 B1 | 11/2002 | Errico |
| 6,482,234 B1 | 11/2002 | Weber et al. |
| 6,488,710 B2 | 12/2002 | Besselink |
| 6,491,724 B1 | 12/2002 | Ferree |
| 6,500,180 B1 | 12/2002 | Foley et al. |
| 6,500,205 B1 | 12/2002 | Michelson |
| 6,500,206 B1 | 12/2002 | Bryan |
| 6,520,996 B1 | 2/2003 | Manasas et al. |
| 6,524,312 B2 | 2/2003 | Landry et al. |
| 6,533,817 B1 | 3/2003 | Norton et al. |
| 6,533,818 B1 | 3/2003 | Weber et al. |
| 6,537,320 B1 | 3/2003 | Michelson |
| 6,540,748 B2 | 4/2003 | Lombardo |
| 6,558,423 B1 | 5/2003 | Michelson |
| 6,558,424 B2 | 5/2003 | Thalgott |
| 6,562,040 B1 | 5/2003 | Wagner et al. |
| 6,562,074 B2 | 5/2003 | Gerbec et al. |
| 6,565,566 B1 | 5/2003 | Wagner et al. |
| 6,565,605 B2 | 5/2003 | Goble et al. |
| 6,569,442 B2 | 5/2003 | Gan et al. |
| 6,572,653 B1 | 6/2003 | Simonson |
| 6,576,016 B1 | 6/2003 | Hochschuler et al. |
| 6,579,318 B2 | 6/2003 | Varga et al. |
| 6,579,319 B2 | 6/2003 | Goble et al. |
| 6,582,467 B1 | 6/2003 | Teitelbaum et al. |
| 6,592,624 B1 | 7/2003 | Fraser et al. |
| 6,595,992 B1 | 7/2003 | Wagner et al. |
| 6,595,998 B2 | 7/2003 | Johnson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,671 B2 | 9/2003 | Landry et al. |
| 6,626,904 B1 | 9/2003 | Jammet et al. |
| 6,626,905 B1 | 9/2003 | Schmiel et al. |
| 6,635,062 B2 | 10/2003 | Ray et al. |
| 6,641,614 B1 | 11/2003 | Wagner et al. |
| 6,648,893 B2 | 11/2003 | Dudasik |
| 6,648,915 B2 | 11/2003 | Sazy |
| 6,648,917 B2 | 11/2003 | Gerbec et al. |
| 6,666,870 B2 | 12/2003 | Dixon et al. |
| 6,666,891 B2 | 12/2003 | Boehm, Jr. et al. |
| 6,679,915 B1 | 1/2004 | Cauthen |
| 6,682,533 B1 | 1/2004 | Dinsdale et al. |
| 6,685,742 B1 | 2/2004 | Jackson |
| 6,692,495 B1 | 2/2004 | Zacouto |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,796 B2 | 4/2004 | Cohen et al. |
| 6,723,126 B1 | 4/2004 | Berry |
| 6,733,531 B1 | 5/2004 | Trieu |
| 6,736,850 B2 | 5/2004 | Davis |
| 6,743,257 B2 | 6/2004 | Castro |
| 6,758,861 B2 | 7/2004 | Ralph et al. |
| 6,773,460 B2 | 8/2004 | Jackson |
| 6,802,844 B2 | 10/2004 | Ferree |
| 6,811,567 B2 | 11/2004 | Reiley |
| 6,821,298 B1 | 11/2004 | Jackson |
| 6,852,129 B2 | 2/2005 | Gerbec et al. |
| 6,863,673 B2 | 3/2005 | Gerbec et al. |
| 6,893,464 B2 | 5/2005 | Kiester |
| 6,896,680 B2 | 5/2005 | Michelson |
| 6,902,580 B2 | 6/2005 | Fallin et al. |
| 6,928,284 B2 | 8/2005 | Palat et al. |
| 6,936,070 B1 | 8/2005 | Muhanna |
| 6,936,071 B1 | 8/2005 | Marnay et al. |
| 6,953,477 B2 | 10/2005 | Berry |
| 6,962,606 B2 | 11/2005 | Michelson |
| 6,964,664 B2 | 11/2005 | Freid et al. |
| 6,966,929 B2 | 11/2005 | Mitchell |
| 6,966,930 B2 | 11/2005 | Arnin et al. |
| 6,974,478 B2 | 12/2005 | Reiley et al. |
| 6,981,989 B1 | 1/2006 | Fleischmann et al. |
| 6,991,632 B2 | 1/2006 | Ritland |
| 6,994,727 B2 | 2/2006 | Khandkar et al. |
| 6,997,929 B2 | 2/2006 | Manzi et al. |
| 7,011,685 B2 | 3/2006 | Arnin et al. |
| 7,018,415 B1 | 3/2006 | McKay |
| 7,029,475 B2 | 4/2006 | Panjabi |
| 7,060,073 B2 | 6/2006 | Frey et al. |
| 7,060,100 B2 | 6/2006 | Ferree |
| 7,083,622 B2 | 8/2006 | Simonson |

(56) References Cited

U.S. PATENT DOCUMENTS

| | | |
|---|---|---|
| 7,083,649 B2 | 8/2006 | Zucherman et al. |
| 7,090,698 B2 | 8/2006 | Goble et al. |
| 7,101,398 B2 | 9/2006 | Dooris et al. |
| 7,118,579 B2 | 10/2006 | Michelson |
| 7,118,580 B1 | 10/2006 | Beyersdorff et al. |
| 7,128,760 B2 | 10/2006 | Michelson |
| 7,147,664 B2 | 12/2006 | Louis et al. |
| 7,153,310 B2 | 12/2006 | Ralph et al. |
| 7,198,644 B2 | 4/2007 | Schultz et al. |
| 7,204,852 B2 | 4/2007 | Marnay et al. |
| 7,204,853 B2 | 4/2007 | Gordon et al. |
| 7,217,291 B2 | 5/2007 | Zucherman et al. |
| 7,270,681 B2 | 9/2007 | Cauthen |
| 7,273,496 B2 | 9/2007 | Mitchell |
| 7,291,150 B2 | 11/2007 | Graf |
| 7,291,159 B2 | 11/2007 | Graf |
| 7,291,173 B2 | 11/2007 | Richelsoph et al. |
| 7,311,713 B2 | 12/2007 | Johnson et al. |
| 7,316,714 B2 | 1/2008 | Gordon et al. |
| 7,318,839 B2 | 1/2008 | Malberg et al. |
| 7,320,707 B2 | 1/2008 | Zucherman et al. |
| 7,326,250 B2 | 2/2008 | Beaurain et al. |
| 7,338,525 B2 | 3/2008 | Ferree |
| 7,338,527 B2 | 3/2008 | Blatt et al. |
| 7,364,589 B2 | 4/2008 | Eisermann |
| 7,473,276 B2 | 1/2009 | Aebi et al. |
| 7,476,238 B2 | 1/2009 | Panjabi |
| 7,485,146 B1 | 2/2009 | Crook et al. |
| 7,517,359 B2 | 4/2009 | Drewry et al. |
| 7,547,309 B2 | 6/2009 | Bertagnoli et al. |
| 7,550,009 B2 | 6/2009 | Arnin et al. |
| 7,556,651 B2 | 7/2009 | Humphreys et al. |
| 7,615,068 B2 | 11/2009 | Timm et al. |
| 7,635,379 B2 | 12/2009 | Callahan et al. |
| 7,682,396 B2 | 3/2010 | Beaurain et al. |
| 7,699,875 B2 | 4/2010 | Timm et al. |
| 7,708,778 B2 | 5/2010 | Gordon et al. |
| 7,713,287 B2 | 5/2010 | Timm et al. |
| 7,713,288 B2 | 5/2010 | Timm et al. |
| 7,727,280 B2 | 6/2010 | McLuen |
| 7,753,958 B2 | 7/2010 | Gordon et al. |
| 7,771,479 B2 | 8/2010 | Humphreys et al. |
| 7,785,351 B2 | 8/2010 | Gordon et al. |
| 7,794,480 B2 | 9/2010 | Gordon et al. |
| 7,799,082 B2 | 9/2010 | Gordon et al. |
| 7,811,309 B2 | 10/2010 | Timm et al. |
| 7,819,801 B2 | 10/2010 | Miles et al. |
| 7,828,849 B2 | 11/2010 | Lim |
| 7,896,919 B2 | 3/2011 | Belliard et al. |
| 7,909,869 B2 | 3/2011 | Gordon et al. |
| 7,909,877 B2 | 3/2011 | Krueger et al. |
| 7,927,374 B2 | 4/2011 | Duggal et al. |
| 7,931,675 B2 | 4/2011 | Panjabi et al. |
| 7,942,905 B2 | 5/2011 | Lim et al. |
| 7,951,170 B2 | 5/2011 | Jackson |
| 7,959,677 B2 | 6/2011 | Landry et al. |
| 8,043,379 B2 | 10/2011 | Moumene et al. |
| 8,052,723 B2 | 11/2011 | Gordon et al. |
| 8,062,375 B2 | 11/2011 | Glerum et al. |
| 8,105,382 B2 | 1/2012 | Olmos et al. |
| 8,118,869 B2 | 2/2012 | Gordon et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,128,700 B2 | 3/2012 | Delurio et al. |
| 8,147,550 B2 | 4/2012 | Gordon et al. |
| 8,157,844 B2 | 4/2012 | Gimbel et al. |
| 8,162,994 B2 | 4/2012 | Gimbel et al. |
| 8,172,903 B2 | 5/2012 | Gordon et al. |
| 8,182,514 B2 | 5/2012 | Gimbel et al. |
| 8,187,330 B2 | 5/2012 | Gimbel et al. |
| 8,257,440 B2 | 9/2012 | Gordon et al. |
| 8,267,965 B2 | 9/2012 | Gimbel et al. |
| 8,303,660 B1 | 11/2012 | Abdou |
| 8,377,098 B2 | 2/2013 | Landry et al. |
| 8,388,687 B2 | 3/2013 | Gimbel et al. |
| 8,398,713 B2 | 3/2013 | Weiman |
| 8,414,652 B2 | 4/2013 | Moumene et al. |
| 8,435,298 B2 | 5/2013 | Weiman |
| 8,475,461 B2 | 7/2013 | Butler et al. |
| 8,486,148 B2 | 7/2013 | Butler et al. |
| 8,491,659 B2 | 7/2013 | Weiman |
| 8,512,407 B2 | 8/2013 | Butler et al. |
| 8,518,120 B2 | 8/2013 | Glerum et al. |
| 8,523,912 B2 | 9/2013 | Gimbel et al. |
| 8,556,979 B2 | 10/2013 | Glerum et al. |
| 8,591,553 B2 | 11/2013 | Eisermann et al. |
| 8,597,358 B2 | 12/2013 | Landry et al. |
| 8,603,168 B2 | 12/2013 | Gordon et al. |
| 8,632,595 B2 | 1/2014 | Weiman |
| 8,647,386 B2 | 2/2014 | Gordon et al. |
| 8,679,183 B2 | 3/2014 | Glerum et al. |
| 8,685,098 B2 | 4/2014 | Glerum et al. |
| 8,709,086 B2 | 4/2014 | Glerum |
| 8,753,398 B2 | 6/2014 | Gordon et al. |
| 8,940,022 B2 | 1/2015 | Landry et al. |
| 8,940,051 B2 | 1/2015 | Gimbel et al. |
| 9,066,811 B2 | 6/2015 | Landry et al. |
| 9,320,610 B2 | 4/2016 | Alheidt et al. |
| 9,717,601 B2 * | 8/2017 | Miller .............. A61F 2/4611 |
| 10,166,117 B1 * | 1/2019 | Daffinson .......... A61B 17/7059 |
| 2001/0020476 A1 | 9/2001 | Gan et al. |
| 2001/0032020 A1 | 10/2001 | Besselink |
| 2002/0040243 A1 | 4/2002 | Atalli et al. |
| 2002/0045945 A1 | 4/2002 | Liu et al. |
| 2002/0065557 A1 | 5/2002 | Goble et al. |
| 2002/0068977 A1 | 6/2002 | Jackson |
| 2002/0072801 A1 | 6/2002 | Michelson |
| 2002/0082701 A1 | 6/2002 | Zdeblick et al. |
| 2002/0091390 A1 | 7/2002 | Michelson |
| 2002/0095154 A1 | 7/2002 | Atkinson et al. |
| 2002/0123806 A1 | 9/2002 | Reiley |
| 2002/0128659 A1 | 9/2002 | Michelson |
| 2002/0128714 A1 | 9/2002 | Manasas et al. |
| 2002/0130112 A1 | 9/2002 | Manasas et al. |
| 2002/0138077 A1 | 9/2002 | Ferree |
| 2002/0143401 A1 | 10/2002 | Michelson |
| 2003/0028250 A1 | 2/2003 | Reiley et al. |
| 2003/0040802 A1 | 2/2003 | Errico |
| 2003/0055427 A1 | 3/2003 | Graf |
| 2003/0065396 A1 | 4/2003 | Michelson |
| 2003/0069643 A1 | 4/2003 | Ralph et al. |
| 2003/0074063 A1 | 4/2003 | Gerbec et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0135275 A1 | 7/2003 | Garcia et al. |
| 2003/0135277 A1 | 7/2003 | Bryan et al. |
| 2003/0139812 A1 | 7/2003 | Gacia et al. |
| 2003/0149483 A1 | 8/2003 | Michelson |
| 2003/0176923 A1 | 9/2003 | Keller et al. |
| 2003/0191470 A1 | 10/2003 | Ritland |
| 2003/0204259 A1 | 10/2003 | Goble et al. |
| 2003/0204260 A1 | 10/2003 | Ferree |
| 2003/0220643 A1 | 11/2003 | Ferree |
| 2003/0225409 A1 | 12/2003 | Freid et al. |
| 2003/0233145 A1 | 12/2003 | Landry et al. |
| 2004/0006391 A1 | 1/2004 | Reiley |
| 2004/0019353 A1 | 1/2004 | Freid et al. |
| 2004/0030387 A1 | 2/2004 | Landry et al. |
| 2004/0030389 A1 | 2/2004 | Ferree |
| 2004/0039448 A1 | 2/2004 | Pisharodi |
| 2004/0044411 A1 | 3/2004 | Suddaby |
| 2004/0049190 A1 | 3/2004 | Biedermann et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |

(56) References Cited

U.S. PATENT DOCUMENTS

| | | |
|---|---|---|
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0087947 A1 | 5/2004 | Lim et al. |
| 2004/0093083 A1 | 5/2004 | Branch et al. |
| 2004/0102774 A1 | 5/2004 | Trieu |
| 2004/0106997 A1 | 6/2004 | Lieberson |
| 2004/0117020 A1 | 6/2004 | Frey et al. |
| 2004/0127989 A1 | 7/2004 | Dooris et al. |
| 2004/0133278 A1 | 7/2004 | Marino et al. |
| 2004/0133281 A1 | 7/2004 | Khandkar et al. |
| 2004/0138662 A1 | 7/2004 | Landry et al. |
| 2004/0138749 A1 | 7/2004 | Zucherman |
| 2004/0143265 A1 | 7/2004 | Landry et al. |
| 2004/0143332 A1 | 7/2004 | Krueger et al. |
| 2004/0147928 A1 | 7/2004 | Landry et al. |
| 2004/0153065 A1 | 8/2004 | Lim |
| 2004/0167626 A1 | 8/2004 | Geremakis et al. |
| 2004/0181223 A1 | 9/2004 | Ritland |
| 2004/0181284 A1 | 9/2004 | Simonson |
| 2004/0220567 A1 | 11/2004 | Eisermann et al. |
| 2004/0236327 A1 | 11/2004 | Paul et al. |
| 2004/0236329 A1 | 11/2004 | Panjabi |
| 2004/0243240 A1 | 12/2004 | Beaurain et al. |
| 2004/0254643 A1 | 12/2004 | Jackson |
| 2004/0254644 A1 | 12/2004 | Taylor |
| 2004/0267364 A1 | 12/2004 | Carli et al. |
| 2004/0267369 A1 | 12/2004 | Lyons et al. |
| 2005/0010295 A1 | 1/2005 | Michelson |
| 2005/0015146 A1 | 1/2005 | Louis et al. |
| 2005/0015149 A1 | 1/2005 | Michelson |
| 2005/0021144 A1 | 1/2005 | Malberg et al. |
| 2005/0027361 A1 | 2/2005 | Reiley |
| 2005/0033432 A1 | 2/2005 | Gordon et al. |
| 2005/0033437 A1 | 2/2005 | Bao et al. |
| 2005/0033439 A1 | 2/2005 | Gordon et al. |
| 2005/0043800 A1 | 2/2005 | Paul et al. |
| 2005/0049590 A1 | 3/2005 | Alleyne et al. |
| 2005/0060034 A1 | 3/2005 | Berry |
| 2005/0085815 A1 | 4/2005 | Harms et al. |
| 2005/0107881 A1 | 5/2005 | Neville et al. |
| 2005/0113927 A1 | 5/2005 | Malek |
| 2005/0124991 A1 | 6/2005 | Jahng |
| 2005/0125061 A1 * | 6/2005 | Zucherman ........... A61F 2/4425 623/17.11 |
| 2005/0125062 A1 | 6/2005 | Biedermann et al. |
| 2005/0131406 A1 | 6/2005 | Reiley |
| 2005/0143818 A1 | 6/2005 | Yuan et al. |
| 2005/0149020 A1 | 7/2005 | Jahng |
| 2005/0149023 A1 | 7/2005 | Ritland |
| 2005/0154461 A1 | 7/2005 | Humphreys et al. |
| 2005/0154462 A1 | 7/2005 | Zucherman et al. |
| 2005/0154465 A1 | 7/2005 | Hodges et al. |
| 2005/0154466 A1 | 7/2005 | Humphreys et al. |
| 2005/0159818 A1 | 7/2005 | Blain |
| 2005/0171543 A1 | 8/2005 | Timm et al. |
| 2005/0171608 A1 | 8/2005 | Peterman et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182401 A1 | 8/2005 | Timm et al. |
| 2005/0182409 A1 | 8/2005 | Callahan et al. |
| 2005/0033431 A1 | 9/2005 | Gordon et al. |
| 2005/0203517 A1 | 9/2005 | Jahng et al. |
| 2005/0209697 A1 | 9/2005 | Paponneau et al. |
| 2005/0209698 A1 | 9/2005 | Gordon et al. |
| 2005/0222569 A1 | 10/2005 | Panjabi |
| 2005/0228500 A1 | 10/2005 | Kim et al. |
| 2005/0245930 A1 | 11/2005 | Timm et al. |
| 2005/0251261 A1 | 11/2005 | Peterman |
| 2005/0256578 A1 | 11/2005 | Blatt et al. |
| 2005/0261771 A1 | 11/2005 | Paul et al. |
| 2005/0117725 A1 | 12/2005 | Parson |
| 2005/0273167 A1 | 12/2005 | Triplett et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288670 A1 | 12/2005 | Panjabi et al. |
| 2006/0009768 A1 | 1/2006 | Ritland |
| 2006/0009850 A1 | 1/2006 | Frigg et al. |
| 2006/0015100 A1 | 1/2006 | Panjabi et al. |
| 2006/0149385 A1 | 1/2006 | McKay |
| 2006/0036240 A1 | 2/2006 | Colleran |
| 2006/0036245 A1 | 2/2006 | Stern |
| 2006/0084986 A1 | 4/2006 | Grinberg et al. |
| 2006/0089717 A1 | 4/2006 | Krishna et al. |
| 2006/0095132 A1 | 5/2006 | Kirschman |
| 2006/0122701 A1 | 6/2006 | Kiester |
| 2006/0129244 A1 | 6/2006 | Ensign |
| 2006/0142759 A1 | 6/2006 | Arnin et al. |
| 2006/0149228 A1 | 7/2006 | Schlapfer et al. |
| 2006/0149229 A1 | 7/2006 | Kwak et al. |
| 2006/0149278 A1 | 7/2006 | Abdou |
| 2006/0149372 A1 | 7/2006 | Paxson et al. |
| 2006/0149383 A1 | 7/2006 | Arnin et al. |
| 2006/0155377 A1 | 7/2006 | Beaurain et al. |
| 2006/0167547 A1 | 7/2006 | Suddaby |
| 2006/0189983 A1 | 8/2006 | Fallin et al. |
| 2006/0195114 A1 | 8/2006 | Bertagnoli |
| 2006/0195191 A1 | 8/2006 | Sweeney et al. |
| 2006/0195192 A1 | 8/2006 | Gordon et al. |
| 2006/0217712 A1 | 9/2006 | Mueller et al. |
| 2006/0229729 A1 | 10/2006 | Gordon |
| 2006/0241642 A1 | 10/2006 | Arnin et al. |
| 2006/0241769 A1 | 10/2006 | Gordon et al. |
| 2006/0241770 A1 | 10/2006 | Rhoda et al. |
| 2006/0241771 A1 | 10/2006 | Gordon et al. |
| 2006/0247635 A1 | 11/2006 | Gordon et al. |
| 2006/0247779 A1 | 11/2006 | Gordon et al. |
| 2006/0253201 A1 | 11/2006 | McLuen |
| 2006/0260483 A1 | 11/2006 | Hartmann et al. |
| 2006/0264937 A1 | 11/2006 | White |
| 2006/0265068 A1 | 11/2006 | Schwab |
| 2006/0265074 A1 | 11/2006 | Krishna |
| 2007/0010886 A1 | 1/2007 | Banick |
| 2007/0073405 A1 | 3/2007 | Verhulst et al. |
| 2007/0073406 A1 | 3/2007 | Gordon et al. |
| 2007/0093828 A1 | 4/2007 | Abdou |
| 2007/0093846 A1 | 4/2007 | Frigg et al. |
| 2007/0162137 A1 | 7/2007 | Kloss et al. |
| 2007/0225814 A1 | 7/2007 | Atkinson |
| 2007/0213720 A1 | 9/2007 | Gordon et al. |
| 2007/0213821 A1 | 9/2007 | Kwak et al. |
| 2007/0239279 A1 | 10/2007 | Francis |
| 2007/0270814 A1 | 11/2007 | Lim et al. |
| 2007/0270838 A1 | 11/2007 | Bruneau et al. |
| 2007/0270972 A1 | 11/2007 | Gordon et al. |
| 2007/0288094 A1 | 12/2007 | Krishna et al. |
| 2008/0015702 A1 | 1/2008 | Lakin et al. |
| 2008/0021285 A1 | 1/2008 | Drzyzga et al. |
| 2008/0027547 A1 | 1/2008 | Yu et al. |
| 2008/0033562 A1 | 2/2008 | Krishna |
| 2008/0065079 A1 | 3/2008 | Bruneau et al. |
| 2008/0133013 A1 | 6/2008 | Duggal et al. |
| 2008/0140207 A1 | 6/2008 | Olmos et al. |
| 2008/0147193 A1 | 6/2008 | Matthis et al. |
| 2008/0161853 A1 | 7/2008 | Arnold et al. |
| 2008/0177310 A1 | 7/2008 | Reiley |
| 2008/0183204 A1 | 7/2008 | Greenhalgh et al. |
| 2008/0234732 A1 | 9/2008 | Landry et al. |
| 2008/0234740 A1 | 9/2008 | Landry et al. |
| 2008/0234741 A1 | 9/2008 | Landry et al. |
| 2008/0234764 A1 | 9/2008 | Landry et al. |

(56) References Cited

U.S. PATENT DOCUMENTS

| | | |
|---|---|---|
| 2008/0234823 A1 | 9/2008 | Landry et al. |
| 2008/0300685 A1 | 12/2008 | Carls et al. |
| 2008/0312692 A1 | 12/2008 | Brennan et al. |
| 2009/0005817 A1 | 1/2009 | Friedrich et al. |
| 2009/0076549 A1 | 3/2009 | Lim et al. |
| 2009/0088847 A1 | 4/2009 | Krishna et al. |
| 2009/0093846 A1 | 4/2009 | Hestad |
| 2009/0105757 A1 | 4/2009 | Gimbel et al. |
| 2009/0105758 A1 | 4/2009 | Gimbel et al. |
| 2009/0105759 A1 | 4/2009 | Gimbel et al. |
| 2009/0105764 A1 | 4/2009 | Jackson |
| 2009/0105820 A1 | 4/2009 | Jackson |
| 2009/0105827 A1 | 4/2009 | Gimbel et al. |
| 2009/0105828 A1 | 4/2009 | Gimbel et al. |
| 2009/0105829 A1 | 4/2009 | Gimbel et al. |
| 2009/0143862 A1 | 6/2009 | Trieu |
| 2009/0177196 A1 | 7/2009 | Zlock et al. |
| 2009/0270870 A1 | 10/2009 | Zubok et al. |
| 2010/0030336 A1 | 2/2010 | Cope |
| 2010/0082109 A1 | 4/2010 | Greenhalgh et al. |
| 2010/0174317 A1 | 7/2010 | Timm et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222819 A1 | 9/2010 | Timm et al. |
| 2010/0222884 A1 | 9/2010 | Greenhalgh |
| 2010/0292796 A1 | 11/2010 | Greenhalgh et al. |
| 2010/0298941 A1 | 11/2010 | Hes et al. |
| 2010/0331985 A1 | 12/2010 | Gordon et al. |
| 2011/0015742 A1 | 1/2011 | Hong |
| 2011/0196428 A1 | 8/2011 | Panjabi et al. |
| 2011/0319997 A1 | 12/2011 | Glerum et al. |
| 2012/0035729 A1 | 2/2012 | Glerum et al. |
| 2012/0059470 A1* | 3/2012 | Weiman .............. A61F 2/447 623/17.11 |
| 2012/0143254 A1 | 6/2012 | Gimbel et al. |
| 2012/0232552 A1 | 9/2012 | Morgenstern Lopez et al. |
| 2012/0245689 A1 | 9/2012 | Gimbel et al. |
| 2012/0265309 A1 | 10/2012 | Glerum et al. |
| 2012/0310349 A1 | 12/2012 | Gordon et al. |
| 2012/0330421 A1 | 12/2012 | Weiman |
| 2013/0023994 A1 | 1/2013 | Glerum |
| 2013/0158667 A1 | 6/2013 | Tabor et al. |
| 2013/0158669 A1 | 6/2013 | Sungarian et al. |
| 2013/0190876 A1 | 7/2013 | Drochner et al. |
| 2013/0204371 A1 | 8/2013 | McLuen et al. |
| 2013/0211525 A1* | 8/2013 | McLuen ............ A61F 2/442 623/17.16 |
| 2013/0211526 A1 | 8/2013 | Alheidt et al. |
| 2013/0245769 A1 | 9/2013 | Gimbel et al. |
| 2014/0067071 A1 | 3/2014 | Man et al. |
| 2014/0277500 A1* | 9/2014 | Logan ............... A61F 2/447 623/17.16 |
| 2018/0200075 A1* | 7/2018 | Baker ............... A61F 2/447 |

FOREIGN PATENT DOCUMENTS

| | | |
|---|---|---|
| FR | 2718946 | 10/1995 |
| FR | 2735351 | 12/1996 |
| FR | 2745706 | 9/1997 |
| FR | 2799949 | 4/2001 |
| RU | 2085145 | 7/1997 |
| WO | WO 98/48739 | 11/1998 |
| WO | WO 2000/004851 | 2/2000 |
| WO | WO 2000/074606 | 12/2000 |
| WO | WO 2001/001893 | 1/2001 |
| WO | WO 2001/056513 | 8/2001 |
| WO | WO 2002/045625 | 6/2002 |
| WO | WO 2004/019762 | 3/2004 |
| WO | WO 2004/019828 | 3/2004 |
| WO | WO 2004/019830 | 3/2004 |
| WO | WO 2004/024011 | 3/2004 |
| WO | WO 2004/026188 | 4/2004 |
| WO | WO 2004/041129 | 5/2004 |
| WO | WO 2004/054479 | 7/2004 |
| WO | WO 2005/016194 | 2/2005 |
| WO | WO 2005/067824 | 7/2005 |
| WO | WO 2005/070349 | 8/2005 |
| WO | WO 2005/117725 | 12/2005 |
| WO | WO 2006/002359 | 1/2006 |
| WO | WO 2006/047587 | 5/2006 |
| WO | WO 2006/057698 | 6/2006 |
| WO | WO 2006/066198 | 6/2006 |
| WO | WO 2006/116851 | 11/2006 |
| WO | WO 2006/119447 | 11/2006 |
| WO | WO 2007/104024 | 9/2007 |
| WO | WO 2008/089350 | 7/2008 |
| WO | WO 2012/134980 | 10/2012 |
| WO | WO 2013/023098 | 2/2013 |

OTHER PUBLICATIONS

Case IPR2015-01721: EX1020: Claim chart—Claims 1 and 2 vs. U.S. Pat. No. 5,782,832 to Larsen et al.

Case IPR2015-01749. EX1002: *Flexuspine, Inc.* v. *Globus Medical Inc.*, U.S. District Court for the Eastern District of Texas, Civil Action No. 15-cv-00201-JRG-KNMFiexuspine, Inc.'s Claim Chart for P.R. 3-1 Infringement Contentions.

Case IPR2015-01749. EX1007: Declaration of Jorge A. Ochoa, P.E.

Case IPR2015-01749. EX1008: Curriculum Vitae of Jorge A. Ochoa, P.E.

Case IPR2015-01749. EX1013: Blumenthal SL, Ohnmeiss DO. Intervertebral cages for degenerative spinal diseases. Spine J. Jui-Aug. 2003;3(4):301-309.

Case IPR2015-01749. EX1014: Dooris AP, Gael VK, Grosland NM, Gilbertson LG, Wilder DG. Load-sharing between anterior and posterior elements in a lumbar motion segment implanted with an artificial disc. Spine (Phila Pa 1976). 2001 ;26(6):E122-129.

Case IPR2015-01749. EX1015: Mayer HM, Wiechert K, Korge A, Oose I. Minimally invasive total disc replacement: surgical technique and preliminary clinical results. Eur Spine J. Oct. 2002;11 Suppi2:S124-30.

Case IPR2015-01749. EX1016: Foley KT, Holly LT, Schwender JD. Minimally invasive lumbar fusion. Spine (Phila Pa 1976). Aug. 1, 2003;28(15 Suppi):S26-35.

Case IPR2015-01749. EX1017: Tropiano P, Huang RC, Girardi FP, Mamay T. Lumbar disc replacement: preliminary results with ProDisc II after a minimum follow-up period of 1 year. J Spinal Disord Tech. Aug. 2003;16(4):362-8.

Case IPR2015-01749. EX1018: Felman Y, Lee S-H, Silvera JR, Gepstein R. Posterior Lumbar Interbody Fusion for Degenerative Disc Disease Using a Minimally Invasive B-Twin Expandable Spinal Spacer: a multicenter study. J Spinal Disord Tech . . . 2003; 16(5):455-460.

Case IPR2015-01749. EX1019: Wagner PC, Bagby GW, Grant BD, Gallina A, Ratzlaff M, SandeR. Surgical stabilization of the equine cervical spine. Vet Surg 1979 8:7-12.

Case IPR2015-01749. EX1020: Weiner BK, Fraser RD. Spine update lumbar interbody cages. Spine. Mar. 1, 1998; 23 (5):634-40.

Case IPR2015-01749. EX1021: Zeegers WS, Bohnen LM, Laaper M, Verhaegen MJ. Artificial disc replacement with the modular type SB Charite III: 2-year results in 50 prospectively studied patients. Eur Spine J. 1999;8 (3):210-217.

Case IPR2015-01749. EX1023: Claim chart: Claim 1 vs. U.S. Pat. No. 6,454,806.

Case IPR2015-01749. EX1024: Claim chart: Claim 1 vs. U.S. Pat. No. 5,782,832 in view of U.S. Patent No. 6,491,724.

Case IPR2015-01749. EX1025: Claim Chart: Claim 5 vs. U.S. Pat. No. 5,522,899.

Case IPR2015-01755: EX1006: Declaration of Jorge A. Ochoa, P.E.

Case IPR2015-01755: EX1018: Claim chart—Claim 23 vs. U.S. Pat. No. 6,595,998.

Case IPR2015-01755: EX1019: Claim chart—Claim 37 vs. U.S. Pat. No. 6,595,998.

(56) References Cited

OTHER PUBLICATIONS

Case IPR2015-01755: EX1020: Claim chart—Claim 37 vs. U.S. Pat. No. 6,176,882.
Case IPR2015-01795: EX1005: Declaration of Jorge A. Ochoa, P.E.
Case IPR2015-01795: EX1017: Claim chart—Claims 1-4 vs. U.S. Pat. No. 6,595,998- Ground 1.
Case IPR2015-01795: EX1018: Claim chart—Claims 1-4 vs. U.S. Pat. No. 6,595,998- Ground 2.
Case IPR2015-01830: EX1006: Declarati_on of Jorge A. Ochoa, P.E.
Case IPR2015-01830: EX1021: Claim chart—Claim 17 vs. U.S. Pat. No. 7,828,849.
Case IPR2015-01830: EX1022: Claim chart—Claim 17 vs. U.S. Pat. No. 6,595,998.
Co-pending U.S. Appl. No. 13/072,511 entitled "Instrumentation for Artificial Functional Spinal Unit System" to Gimbel et al., filed Mar. 25, 2011.
Co-pending U.S. Appl. No. 13/437,604 entitled "Method of Inserting an Expandable Intervertebral Implant Without Overdistraction" to Gordon et al., filed Apr. 2, 2012.
Co-pending U.S. Appl. No. 13/784,224 entitled "Interbody Device Insertion Systems and Methods" to Gimbel et al., filed Mar. 4, 2013.
Co-pending U.S. Appl. No. 13/306,535 entitled "Posterior Stabilization Systems With Shared, Dual Dampener Systems" to Gimbel et al., filed Nov. 29, 2011.
Co-pending U.S. Appl. No. 13/967,776 entitled "Expandable Intervertebral Implant" to Gordon et al., filed Aug. 15, 2013.
Co-pending U.S. Appl. No. 14/185,561 entitled "Expandable Fusion Device for Positioning Between Adjacent Vertebral Bodies" to Wagner, filed Feb. 20, 2014.
E.P. Communication Pursuant to Article 94(3) EPC for Application No. 08713804.6-2310 dated Dec. 5, 2013.
E.P. Communication Pursuant to Article 94(3) EPC for Application No. 08713804.6-2310 dated Jan. 22, 2013.
E.P.O. Communication Pursuant to Article 94(3) for European Application No. 07 758 171.8 dated Feb. 26, 2013.
E.P.O. Communication Pursuant to Article 94(3) for European Application No. 07 758 171.8-2310 dated Oct. 11, 2012.
E.P.O. Decision to Grant for European Application No. 07 758 171.8 dated May 30, 2014.
E.P.O. Notice of Intent to Grant for European Application No. 07 758 171.8 dated Feb. 26, 2013.
E.P.O. Report of Deficiencies for European Application No. 07 758 171.8-2310 dated Feb. 13, 2012.
Hodges et al., "Biomechanics of the Kenti (TM) Total Joint Replacement", Presented at the Global Symposium on Motion Preservation Technology, May 9-13, 2006; 1 page.
Humphreys et al., "Biomechanics of the KENTI (TM) Total Joint Replacement", Presented at the Global Symposium on Motion Preservation Technology, May 9-13, 2006; 3 pages.
International Preliminary Report on Patentability for International Application No. PCT/US2008/051346 dated Mar. 27, 2009, 23 pages.
International Preliminary Report on Patentability for International Application No. PCT/US2012/030248 dated Oct. 23, 2012, 11 pages.
International Search Report and Written Opinion for International Application No. PCT/US2008/051346 dated Sep. 9, 2008, 20 pages.
J.P. Final Decision of Rejection for Japanese Application No. 2008-558536 considered by Examiner dated Sep. 4, 2012.
J.P. Notice of Reason for Refusal for Japanese Application No. 2008-558536 considered by Examiner dated Jan. 12, 2012. Attorney Docket No. 5943-00907.
J.P. Notice of Reason for Refusal for Japanese Application No. 2009-546510 dated Mar. 6, 2012.
J.P. Notice of Reason for Refusal for Japanese Application No. 2009-546510 dated Oct. 9, 2012.
Khoueir et al. "Classification of posterior dynamic stabilization devices," Neurosurg Focus, 2007, 22(1):E1, 8 pages.
Patel et al., "Changes in Kinematics following Single Level fusion, Single and Bi-Level Charite disc replacement in the Lumbar Spine" Presented at the Global Symposium on Motion Preservation Technology, May 9-13, 2006; 1 page.
PCT Search Report and Written Opinion for International Application No. PCT/US2007/063595 dated Dec. 11, 2007, 15 pages.
PCT Search Report and Written Opinion for PCT/US2004/025090 dated Apr. 11, 2005 (23 pages).
Petition for Inter Partes Review of U.S. Pat. No. 7,204,853 filed Aug. 17, 2015. Petitioner: *Globus Medical, Inc.* v. Patent Owner: *Flexuspine, Inc.* Case IPR2015-01749.
Petition for Inter Partes Review of U.S. Pat. No. 7,316,714 filed Aug. 14, 2015. Petitioner: *Globus Medical, Inc.* v. Patent Owner: *Flexuspine, Inc.* Case IPR2015-01721.
Petition for Inter Partes Review of U.S. Pat. No. 7,909,869 filed Aug. 18, 2015. Petitioner: *Globus Medical, Inc.* v. Patent Owner: *Flexuspine, Inc.* Case IPR2015-01755.
Petition for Inter Partes Review of U.S. Pat. No. 8,647,386 filed Aug. 24, 2015. Petitioner: *Globus Medical, Inc.* v. Patent Owner: *Flexuspine, Inc.* Case IPR2015-01795.
Petition for Inter Partes Review of U.S. Patent No. 8, 123,810 filed Aug. 27, 2015. Petitioner: *Globus Medical, Inc.* v. Patent Owner: *Flexuspine, Inc.* Case IPR2015-01830.
Serhan et al. "Biomechanics of the posterior lumbar articulating elements," Neurosurg Focus 2007, 22(1):E1, 6 pages.
U.S. Patent and Trademark Office "Communication" for U.S. Appl. No. 10/777,411 dated Aug. 29, 2008.
U.S. Patent and Trademark Office "Communication" for U.S. Appl. No. 10/777,411 dated Dec. 23, 2008.
U.S. Patent and Trademark Office "Communication" for U.S. Appl. No. 10/777,411 dated Mar. 19, 2007.
U.S. Patent and Trademark Office "Communication" for U.S. Appl. No. 10/777,411 dated Mar. 20, 2008.
U.S. Patent and Trademark Office "Communication" for U.S. Appl. No. 10/777,411 dated Sep. 24, 2007.
U.S. Patent and Trademark Office "Communication" for U.S. Appl. No. 10/777,411, dated Jul. 17, 2009.
U.S. Patent and Trademark Office "Communication" for U.S. Appl. No. 10/777,411, dated Jun. 9, 2010.
U.S. Patent and Trademark Office "Communication" for U.S. Appl. No. 10/777,411, dated Mar. 5, 2010.
U.S. Patent and Trademark Office "Communication" for U.S. Appl. No. 10/777,411, dated Oct. 1, 2009.
U.S. Patent and Trademark Office "Communication" for U.S. Appl. No. 10/777,411, dated Oct. 15, 2010.
U.S. Patent and Trademark Office "Communication" for U.S. Appl. No. 11/050,632 dated Apr. 6, 2009.
U.S. Patent and Trademark Office "Communication" for U.S. Appl. No. 11/050,632 dated Sep. 24, 2008.
U.S. Patent and Trademark Office "Communication" for U.S. Appl. No. 11/050,632, dated Aug. 25, 2009.
U.S. Patent and Trademark Office "Communication" for U.S. Appl. No. 11/050,632, dated Mar. 2, 2010.
U.S. Patent and Trademark Office "Communication" for U.S. Appl. No. 11/134,055 dated Aug. 25, 2008.
U.S. Patent and Trademark Office "Communication" for U.S. Appl. No. 11/134,055, dated Jan. 19, 2010.
U.S. Patent and Trademark Office "Communication" for U.S. Appl. No. 11/134,066 dated Dec. 4, 2008.
U.S. Patent and Trademark Office "Communication" for U.S. Appl. No. 11/134,066, dated Feb. 18, 2010.
U.S. Patent and Trademark Office "Communication" for U.S. Appl. No. 11/134,066, dated Sep. 9, 2009.
U.S. Patent and Trademark Office "Communication" for U.S. Appl. No. 11/134,067, dated Aug. 14, 2009.
U.S. Patent and Trademark Office "Communication" for U.S. Appl. No. 11/134,067, dated Feb. 18, 2010.
U.S. Patent and Trademark Office "Communication" for U.S. Appl. No. 11/134,069 dated Dec. 24, 2008.
U.S. Patent and Trademark Office "Communication" for U.S. Appl. No. 11/134,069 dated Jun. 5, 2009.
U.S. Patent and Trademark Office "Communication" for U.S. Appl. No. 11/134,069, dated Apr. 19, 2010.

(56) References Cited

OTHER PUBLICATIONS

U.S. Patent and Trademark Office "Communication" for U.S. Appl. No. 11/134,069, dated Dec. 30, 2009.
U.S. Patent and Trademark Office "Communication" for U.S. Application No. 11 /134,073, dated Jan. 27, 2010.
U.S. Patent and Trademark Office "Communication" for U.S. Appl. No. 11/134,073, dated Jul. 22, 2009.
U.S. Patent and Trademark Office "Communication" for U.S. Appl. No. 11/134,079, dated Aug. 14, 2009.
U.S. Patent and Trademark Office "Communication" for U.S. Appl. No. 11/134,079, dated Feb. 19, 2010.
U.S. Patent and Trademark Office "Communication" for U.S. Appl. No. 11/134,082 dated Dec. 3, 2008.
U.S. Patent and Trademark Office "Communication" for U.S. Appl. No. 11/134,082, dated Aug. 14, 2009.
U.S. Patent and Trademark Office "Communication" for U.S. Appl. No. 11/134,082, dated Mar. 12, 2010.
U.S. Patent and Trademark Office "Communication" for U.S. Appl. No. 11/134,082, dated May 25, 2010.
U.S. Patent and Trademark Office "Communication" for U.S. Appl. No. 11/134,091 dated Dec. 24, 2008.
U.S. Patent and Trademark Office "Communication" for U.S. Appl. No. 11/134,091 dated Feb. 21, 2008.
U.S. Patent and Trademark Office "Communication" for U.S. Appl. No. 11/134,091, dated Aug. 4, 2010.
U.S. Patent and Trademark Office "Communication" for U.S. Appl. No. 11 /134,091, dated Jan. 26, 2010.
U.S. Patent and Trademark Office "Communication" for U.S. Appl. No. 11/134,092 dated Feb. 21, 2008.
U.S. Patent and Trademark Office "Communication" for U.S. Appl. No. 11/343,933 dated Jun. 30, 2008.
U.S. Patent and Trademark Office "Communication" for U.S. Appl. No. 11/343,933 dated Nov. 19, 2007.
U.S. Patent and Trademark Office "Communication" for U.S. Appl. No. 11/345,602 dated Mar. 31, 2009.
U.S. Patent and Trademark Office "Communication" for U.S. Appl. No. 11/345,602, dated Oct. 13, 2009.
U.S. Patent and Trademark Office "Communication" for U.S. Appl. No. 11/371,170, dated Jan. 28, 2011.
U.S. Patent and Trademark Office "Communication" for U.S. Appl. No. 11/371,170, dated Jul. 12, 2010.
U.S. Patent and Trademark Office "Communication" for U.S. Appl. No. 11/371,170, dated May 6, 2011.
U.S. Patent and Trademark Office "Communication" for U.S. Appl. No. 11/371,170, dated May 4, 2010.
U.S. Patent and Trademark Office "Communication" for U.S. Appl. No. 11/371,170, dated Nov. 4, 2009.
U.S. Patent and Trademark Office "Communication" for U.S. Appl. No. 11/371,181, dated Oct. 11, 2007.
U.S. Patent and Trademark Office "Communication" for U.S. Appl. No. 11/371,182, dated Apr. 24, 2009.
U.S. Patent and Trademark Office "Communication" for U.S. Appl. No. 11/371,182, dated Aug. 25, 2010.
U.S. Patent and Trademark Office "Communication" for U.S. Appl. No. 11/371,182, dated Dec. 12, 2008.
U.S. Patent and Trademark Office "Communication" for U.S. Appl. No. 11/371,182, dated Feb. 8, 2010.
U.S. Patent and Trademark Office "Communication" for U.S. Appl. No. 11/371,182, dated Jul. 21, 2009.
U.S. Patent and Trademark Office "Communication" for U.S. Appl. No. 11/371,182, dated Jun. 8, 2010.
U.S. Patent and Trademark Office "Communication" for U.S. Appl. No. 11/371,182, dated Jun. 9, 2008.
U.S. Patent and Trademark Office "Communication" for U.S. Appl. No. 11/371,182, dated Mar. 25, 2009.
U.S. Patent and Trademark Office "Communication" for U.S. Appl. No. 11/371,182, dated Oct. 11, 2007.
U.S. Patent and Trademark Office "Communication" for U.S. Appl. No. 11/371,182, dated Oct. 14, 2009.
U.S. Patent and Trademark Office "Communication" for U.S. Appl. No. 11/371,188, dated Apr. 28, 2010.
U.S. Patent and Trademark Office "Communication" for U.S. Appl. No. 11/371,188, dated Jun. 15, 2010.
U.S. Patent and Trademark Office "Communication" for U.S. Appl. No. 11/371,188, dated Mar. 17, 2009.
U.S. Patent and Trademark Office "Communication" for U.S. Appl. No. 11/371,188, dated Sep. 1, 2010.
U.S. Patent and Trademark Office "Communication" for U.S. Appl. No. 11/371,188, dated Sep. 25, 2009.
U.S. Patent and Trademark Office "Communication" for U.S. Appl. No. 11/371,190, dated Apr. 29, 2009.
U.S. Patent and Trademark Office "Communication" for U.S. Appl. No. 11/371,190, dated Apr. 17, 2008.
U.S. Patent and Trademark Office "Communication" for U.S. Appl. No. 11/371,190, dated Aug. 11, 2008.
U.S. Patent and Trademark Office "Communication" for U.S. Appl. No. 11/371,190, dated Aug. 11, 2010.
U.S. Patent and Trademark Office "Communication" for U.S. Appl. No. 11/371,190, dated Feb. 26, 2010.
U.S. Patent and Trademark Office "Communication" for U.S. Appl. No. 11/371,190, dated Nov. 7, 2008.
U.S. Patent and Trademark Office "Communication" for U.S. Appl. No. 11/371,190, dated Oct. 11, 2007.
U.S. Patent and Trademark Office "Communication" for U.S. Appl. No. 11/371,190, dated Oct. 29, 2009.
U.S. Patent and Trademark Office "Communication" for U.S. Appl. No. 11/371,328, dated Dec. 30, 2009.
U.S. Patent and Trademark Office "Communication" for U.S. Appl. No. 11/371,328, dated Jan. 6, 2011.
U.S. Patent and Trademark Office "Communication" for U.S. Appl. No. 11/371,328, dated Jun. 17, 2010.
U.S. Patent and Trademark Office "Communication" for U.S. Appl. No. 11/371,328, dated Mar. 17, 2009.
U.S. Patent and Trademark Office "Communication" for U.S. Appl. No. 11/371,328, dated Sep. 28, 2009.
U.S. Patent and Trademark Office "Communication" for U.S. Appl. No. 11/371,376, dated Apr. 20, 2009.
U.S. Patent and Trademark Office "Communication" for U.S. Appl. No. 11/371,376, dated Aug. 28, 2009.
U.S. Patent and Trademark Office "Communication" for U.S. Appl. No. 11/371,376, dated Jul. 29, 2010.
U.S. Patent and Trademark Office "Communication" for U.S. Appl. No. 11/371,376, dated May 26, 2010.
U.S. Patent and Trademark Office "Communication" for U.S. Appl. No. 11/371,376, dated Nov. 29, 2007.
U.S. Patent and Trademark Office "Communication" for U.S. Appl. No. 11/371,376, dated Nov. 4, 2009.
U.S. Patent and Trademark Office "Communication" for U.S. Appl. No. 11/526,849, dated Dec. 6, 2010.
U.S. Patent and Trademark Office "Communication" for U.S. Appl. No. 11/526,849, dated Feb. 23, 2011.
U.S. Patent and Trademark Office "Communication" for U.S. Application No. 11 /526,849, dated Jun. 1, 2010.
U.S. Patent and Trademark Office "Communication" for U.S. Appl. No. 11/655,723, dated May 27, 2009.
U.S. Patent and Trademark Office "Communication" for U.S. Appl. No. 11/655,723, dated Nov. 24, 2009.
U.S. Patent and Trademark Office "Communication" for U.S. Appl. No. 11/655,724, dated May 27, 2009.
U.S. Patent and Trademark Office "Communication" for U.S. Appl. No. 11/655,737, dated May 27, 2009.
U.S. Patent and Trademark Office "Communication" for U.S. Appl. No. 11/655,724, dated Nov. 23, 2009.
U.S. Patent and Trademark Office "Communication" for U.S. Appl. No. 11/655,737, dated Nov. 23, 2009.
U.S. Patent and Trademark Office "Communication" for U.S. Appl. No. 11/655,787, dated May 27, 2009.
U.S. Patent and Trademark Office "Communication" for U.S. Appl. No. 11/655,787, dated Nov. 23, 2009.
U.S. Patent and Trademark Office "Communication" for U.S. Appl. No. 11/655,790, dated Jun. 4, 2009.

(56) References Cited

OTHER PUBLICATIONS

U.S. Patent and Trademark Office "Communication" for U.S. Appl. No. 11/655,790, dated Mar. 15, 2010.
U.S. Patent and Trademark Office "Communication" for U.S. Appl. No. 11/975,916, dated Aug. 4, 2010.
U.S. Patent and Trademark Office "Communication" for U.S. Appl. No. 11/975,916, dated Feb. 9, 2011.
U.S. Patent and Trademark Office "Communication" for U.S. Appl. No. 11/975,917, dated Aug. 17, 2010.
U.S. Patent and Trademark Office "Communication" for U.S. Appl. No. 11/975,917, dated Feb. 4, 2011.
U.S. Patent and Trademark Office "Communication" for U.S. Application No. 11/975,919, dated Aug. 19, 2010.
U.S. Patent and Trademark Office "Communication" for U.S. Appl. No. 11/975,919, dated Feb. 4, 2011.
U.S.P.T.O. Non-Final Office Action for U.S. Appl. No. 11/655,737, dated Mar. 15, 2013.
U.S.P.T.O. Non-Final Office Action for U.S. Appl. No. 11/975,918, dated Aug. 15, 2011.
U.S.P.T.O. Advisory Action for U.S. Appl. No. 11/134,055, dated Feb. 15, 2012.
U.S.P.T.O. Advisory Action for U.S. Appl. No. 11/134,055, dated Jul. 8, 2013.
U.S.P.T.O. Advisory Action for U.S. Appl. No. 11/371,170, dated Aug. 5, 2011.
U.S.P.T.O. Advisory Action for U.S. Appl. No. 12/841,792, dated Jul. 19, 2012
U.S.P.T.O. Advisory Action for U.S. Appl. No. 13/306,535, dated Sep. 9, 2013.
U.S.P.T.O. Final Office Action for U.S. Appl. No. 11/134,055, dated Apr. 18, 2013.
U.S.P.T.O. Final Office Action for U.S. Appl. No. 11/134,055, dated Nov. 14, 2011.
U.S.P.T.O. Final Office Action for U.S. Appl. No. 11/134,091, dated Feb. 10, 2012.
U.S.P.T.O. Final Office Action for U.S. Appl. No. 11/345,602, dated Aug. 13, 2012.
U.S.P.T.O. Final Office Action for U.S. Appl. No. 11/371,376, dated Oct. 16, 2012.
U.S.P.T.O. Final Office Action for U.S. Appl. No. 11/655,723, dated Dec. 26, 2014.
U.S.P.T.O. Final Office Action for U.S. Appl. No. 11/655,724, dated Aug. 24, 2012.
U.S.P.T.O. Final Office Action for U.S. Appl. No. 11/975,916, dated Sep. 6, 2011.
U.S.P.T.O. Final Office Action for U.S. Appl. No. 11/975,919, dated Jan. 27, 2012.
U.S.P.T.O. Final Office Action for U.S. Appl. No. 12/841,792, dated Mar. 23, 2012.
U.S.P.T.O. Final Office Action for U.S. Appl. No. 13/306,535, dated Jul. 18, 2013.
U.S.P.T.O. Non-Final Office Action for U.S. Appl. No. 10/634,950, dated Dec. 1, 2005.
U.S.P.T.O. Non-Final Office Action for U.S. Appl. No. 11/134,055, dated Jun. 9, 2011.
U.S.P.T.O. Non-Final Office Action for U.S. Appl. No. 11/134,055, dated Nov. 8, 2012.
U.S.P.T.O. Non-Final Office Action for U.S. Appl. No. 11/134,091, dated Aug. 12, 2011.
U.S.P.T.O. Non-Final Office Action for U.S. Appl. No. 11/345,602, dated Mar. 5, 2012.
U.S.P.T.O. Non-Final Office Action for U.S. Appl. No. 11/371,376, dated Mar. 23, 2012.
U.S.P.T.O. Non-Final Office Action for U.S. Appl. No. 11/655,723, dated May 20, 2014.
U.S.P.T.O. Non-Final Office Action for U.S. Appl. No. 11/655,724, dated Feb. 17, 2012.
U.S.P.T.O. Non-Final Office Action for U.S. Appl. No. 11/655,787, dated May 20, 2014.
U.S.P.T.O. Non-Final Office Action for U.S. Appl. No. 11/975,917, dated Aug. 3, 2011.
U.S.P.T.O. Non-Final Office Action for U.S. Appl. No. 11/975,919, dated Jul. 21, 2011.
U.S.P.T.O. Non-Final Office Action for U.S. Appl. No. 11/975,920, dated Jun. 7, 2011.
U.S.P.T.O. Non-Final Office Action for U.S. Appl. No. 11/975,921, dated Jun. 9, 2011.
U.S.P.T.O. Non-Final Office Action for U.S. Appl. No. 12/841,792, dated Oct. 20, 2011.
U.S.P.T.O. Non-Final Office Action for U.S. Appl. No. 13/306,535, dated Aug. 24, 2012.
U.S.P.T.O. Non-Final Office Action for U.S. Appl. No. 13/306,535, dated May 24, 2012.
U.S.P.T.O. Non-Final Office Action for U.S. Appl. No. 13/437,604, dated Jul. 2, 2014.
U.S.P.T.O. Non-Final Office Action for U.S. Appl. No. 14/185,561, dated May 5, 2015.
U.S.P.T.O. Notice of Allowance for U.S. Appl. No. 11/134,055, dated Feb. 19, 2014.
U.S.P.T.O. Notice of Allowance for U.S. Appl. No. 11/134,055, dated May 5, 2014.
U.S.P.T.O. Notice of Allowance for U.S. Appl. No. 11/134,067, dated Oct. 3, 2011.
U.S.P.T.O. Notice of Allowance for U.S. Appl. No. 11/134,069, dated Oct. 13, 2011.
U.S.P.T.O. Notice of Allowance for U.S. Appl. No. 11/134,073, dated Oct. 13, 2011.
U.S.P.T.O. Notice of Allowance for U.S. Appl. No. 11/134,079, dated Nov. 25, 2011.
U.S.P.T.O. Notice of Allowance for U.S. Appl. No. 11/134,082, dated Jan. 11, 2012.
U.S.P.T.O. Notice of Allowance for U.S. Appl. No. 11/134,091, dated May 4, 2012.
U.S.P.T.O. Noticeof Allowance for U.S. Appl. No. 11/371,170, dated Oct. 12, 2011.
U.S.P.T.O. Notice of Allowance for U.S. Appl. No. 11/371,328, dated Jun. 23, 2011.
U.S.P.T.O. Notice of Allowance for U.S. Appl. No. 11/655,723, dated Dec. 26, 2014.
U.S.P.T.O. Notice of Allowance for U.S. Appl. No. 11/655,724, dated Oct. 4, 2012.
U.S.P.T.O. Notice of Allowance for U.S. Appl. No. 11/655,787, dated Sep. 26, 2014.
U.S.P.T.O. Notice of Allowance for U.S. Appl. No. 11/655,790, dated Feb. 4, 2011.
U.S.P.T.O. Notice of Allowance for U.S. Appl. No. 11/975,916, dated Jan. 28, 2013.
U.S.P.T.O. Notice of Allowance for U.S. Appl. No. 11/975,917, dated Feb. 1, 2012.
U.S.P.T.O. Notice of Allowance for U.S. Appl. No. 11/975,918, dated Jan. 19, 2012.
U.S.P.T.O. Notice of Allowance for U.S. Appl. No. 11/975,919, dated May 11, 2012.
U.S.P.T.O. Notice of Allowance for U.S. Appl. No. 11/975,920, dated Nov. 16, 2011.
U.S.P.T.O. Notice of Allowance for U.S. Appl. No. 11/975,921, dated Dec. 14, 2011.
U.S.P.T.O. Notice of Allowance for U.S. Appl. No. 13/784,224 dated Sep. 18, 2014.
U. S. P. T. 0. Non-Final Office Action for U.S. Appl. No. 11/655,723, dated May 20, 2014.
U. S. P. T. 0. Non-Final Office Action for U.S. Appl. No. 13/437,604, dated Jul. 2, 2014.
U. S. P. T. 0. Non-Final Office Action for U.S. Appl. No. 13/437,604, dated Oct. 10, 2014.

* cited by examiner

EXPANDABLE FUSION DEVICE FOR POSITIONING BETWEEN ADJACENT VERTEBRAL BODIES

REFERENCE TO PENDING PRIOR PATENT APPLICATIONS

This patent application is a continuation of pending prior U.S. patent application Ser. No. 15/351,943, filed Nov. 15, 2016 by Flexuspine, Inc. for EXPANDABLE FUSION DEVICE FOR POSITIONING BETWEEN ADJACENT VERTEBRAL BODIES, which in turn is a continuation of prior U.S. patent application Ser. No. 14/185,561, filed Feb. 20, 2014 by Erik Wagner et al. for EXPANDABLE FUSION DEVICE FOR POSITIONING BETWEEN ADJACENT VERTEBRAL BODIES, which claims benefit of prior U.S. Provisional Patent Application Ser. No. 61/766,982, filed Feb. 20, 2013 by Erik Wagner et al. for EXPANDABLE FUSION DEVICE FOR POSITIONING BETWEEN ADJACENT VERTEBRAL BODIES.

The three (3) above-identified patent applications are hereby incorporated herein by reference.

BACKGROUND OF THE INVENTION

1. Field of the Invention

This invention relates to spinal implant devices and methods for promoting fusion between adjacent vertebral bodies, and more particularly to expandable fusion devices that can be inserted between adjacent vertebral bodies to facilitate the fusion thereof.

2. Description of the Relevant Art

The human spine is a complex mechanical structure, composed of alternating bony vertebrae and fibrocartilaginous discs that are connected by strong ligaments and supported by musculature, that extends from the skull to the pelvis and provides axial support for the body.

The vertebrae generally comprise a vertebral foramen bounded by the anterior vertebral body and the neural arch. The vertebral body comprises two end plates (i.e., superior and inferior) made of thin cartilage overlying a thin layer of hard cortical bone that attaches to the spongy, cancellous interior bone of the vertebral body. The neural arch consists of two pedicles and two lamina that are united posteriorly. The spinous and transverse processes protrude from the neural arch. The superior and inferior articular facets lie at the root of the transverse processes.

The intervertebral discs primarily serve as a mechanical cushion between adjacent vertebral segments of the spinal column and generally comprise two basic components: the annulus fibrosis and the nucleus pulposus. The annulus fibrosis forms the outer perimeter of the disc and is a tough ring that binds adjacent vertebrae together. The nucleus pulposus fills the interior of the disc and carries load.

The spine as a whole is a highly flexible structure capable of a high degree of curvature and twist in nearly every direction. However, genetic or developmental irregularities, trauma, chronic stress, and degenerative wear can result in spinal pathologies for which surgical intervention may be necessary.

It is common practice to remove a spinal disc in cases of spinal disc deterioration, disease or spinal injury. More particularly, the discs sometimes become diseased or damaged such that the height of the disc is reduced, which causes the annulus to buckle in areas where the laminated plies are loosely bonded. As the overlapping laminated plies of the annulus begin to buckle and separate, circumferential and/or radial annular tears may occur, allowing nucleus material to escape or form a bulge in the annulus. Such disruption to the natural intervertebral separation and the resulting herniation produces pain, which can be alleviated by removal of the disc and restoration of the natural separation distance. In cases of chronic back or leg pain resulting from a degenerated or herniated disc, removal of the disc can become the desired course of treatment.

In some cases it is desired to fuse the adjacent vertebrae together after removal of the disc. Such a procedure is sometimes referred to as "intervertebral fusion" or "interbody fusion".

Many techniques and instruments have been devised to perform intervertebral fusion. There is common agreement that the strongest intervertebral fusion is interbody fusion between the lumbar bodies, which may be augmented by a posterior or facet fusion. In cases of intervertebral fusion, either structural bone, or a rigid interbody fusion "cage" typically filled with morselized bone, is placed centrally within the space where the spinal disc once resided. Multiple bony grafts or cages may be used within that space. Furthermore, multiple surgical approaches may be utilized, including anterior, posterior, or lateral surgical approaches.

Such practices are characterized by certain disadvantages, including the need to distract the disc space in order to implant the fusion device and thereby restore the diseased disc space to its normal or healthy height. However, it can be difficult to distract the adjacent vertebral bodies sufficiently to easily insert the fusion device between adjacent vertebral bodies. As a result, it is often necessary to drive the fusion device into the space between the vertebral bodies using impaction with a mallet and the application of significant force. The use of such impaction and force increases the risk of damage to local soft tissue such as blood vessels and the surrounding nerves, and can lead to suboptimal placement and/or failure of the insertion instrumentation. Furthermore, the use of such impaction and force can damage or compromise the vertebral endplates, resulting in eventual failure and subsidence of the fusion device into the vertebral bodies and hence loss of disc height.

Therefore, there is a need for a fusion device that can be placed between adjacent vertebral bodies at minimal height and, thereafter, be variably adjusted with minimal force application to the preferred height for an individual patient. Furthermore, it is desirable that the expandable fusion device be maintained in a closed (i.e., unexpanded) position during insertion and handling, and that it be rigidly attachable to a holder so as to facilitate maximum control by the surgeon during insertion and deployment.

SUMMARY

Accordingly, there is now provided an expandable fusion device that can be placed between adjacent vertebral bodies at minimal height and, thereafter, be variably adjusted with minimal force application to the preferred height for an individual patient. In one embodiment, an expandable PLIF (Posterior Lumbar Interbody Fusion) device or an expandable TLIF (Transforaminal Lumbar Interbody Fusion) device, is disclosed. The expandable fusion device generally includes: a cage, superior and lower bodys, and an expansion mechanism with opposing proximal and second expansion members. The application of torque to the expansion mechanism in one direction causes the proximal and second expansion members to separate, whereby to move the superior and lower bodies away from one another and hence increase the height of expandable fusion device 5. The application of torque to the expansion mechanism in the opposite direction causes the proximal and second expansion members to approach one another, whereby to move the superior and lower bodys toward one another and hence decrease the height of the expandable fusion device.

Further embodiments may include: (i) angled or lordotic superior and lower bodys to match the angle of the disc space; (ii) mismatched proximal and second expansion members, such that the anterior portion of the expandable fusion device opens more than the posterior portion of the expandable fusion device, thereby resulting in a fusion device that increases in both height and lordosis; (iii) dual or multiple expansion mechanisms for anterior spinal approaches; (iv) a curved or flexible holder for the expandable fusion device for oblique access approaches; and (v) additional angled components (i.e., intermediate the aforementioned proximal and second expansion members) for longer expandable fusion devices.

In some embodiments, system and/or method may include an intervertebral implant for a human spine including an upper body, a lower body, first and second expansion members, and an expansion mechanism. The upper body may include an inferior surface and a superior surface. The superior surface of the upper body may function to engage a first vertebra of the human spine. The lower body may include a superior surface and an inferior surface. The inferior surface of the lower body may function to engage a second vertebra of the human spine. The first expansion member may include at least a first angled portion. The first angled portion may be positionable, during use, between the inferior surface of the upper body and the superior surface of the lower body. At least the first angled portion may be oriented towards a first end of the intervertebral implant. The second expansion member may include at least a second angled portion positionable, during use, between the inferior surface of the upper body and the superior surface of the lower body. At least the second angled portion may be oriented towards a second end of the intervertebral implant. At least the second angled portion may be oriented in an opposing direction relative to at least the first angled portion. An expansion mechanism may convey, during use, the first and second angled portions in opposing directions increasing a separation distance between the upper body and the lower body. The first and/or second angled portion may include a wedge-shaped portion.

In some embodiments, the expansion mechanism may include a threaded elongated member. The threaded elongated member may include a proximally threaded portion. The first expansion member may include a threaded opening which the threaded portion of the elongated member engages, during use.

In some embodiments, a distal end of the elongated member engages, during use, a proximal end of the second expansion member. The distal end may engage a recess in the second expansion member and rotates freely within it.

In some embodiments, the expansion mechanism may include a first elongated member and a second elongated member. The first elongated member may include a proximally threaded portion. The first expansion member may include a threaded opening which the threaded portion of the first elongated member engages, during use. The second elongated member may be positionable, during use, in an opening in the second expansion member. A distal end of the first elongated member may engage, during use, a proximal end of the second elongated member. In some embodiments, a distal end of the first elongated member may engage, during use, a proximal end of the second elongated member such that the distal end of the first elongated member is positioned in the opening in the second expansion member.

In some embodiments, the expansion member may include a locking member. The locking member may be positionable in the second expansion member such that the distal end of the first elongated member is inhibited, during use, from removal from the opening in the second expansion member.

In some embodiments, the intervertebral implant may include a cage. The cage may form a perimeter around the intervertebral implant in which at least portions of the upper body, the lower body, the first expansion member, the second expansion member, and the expansion mechanism are positioned, during use, in the cage. The cage may include one or more openings along the perimeter to allow graft material to be positioned during use.

In some embodiments, a lateral cross section of a perimeter of the intervertebral implant may include a curved shape such that at least a first portion of the perimeter is substantially convex and at least a second portion of the perimeter is substantially concave, wherein the second portion is substantially opposite the first portion.

In some embodiments, the upper body and/or the lower body may include an opening wherein graft material is positionable during use. The upper body and/or the lower body may include an opening which increases in size as the first and second angled portions are conveyed in opposing directions.

In some embodiments, the superior surface of the upper body and/or the inferior surface of the lower body may include protrusions (e.g., teeth). The protrusions may promote, during use, retention of the implant between the first vertebra and the second vertebra after insertion.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
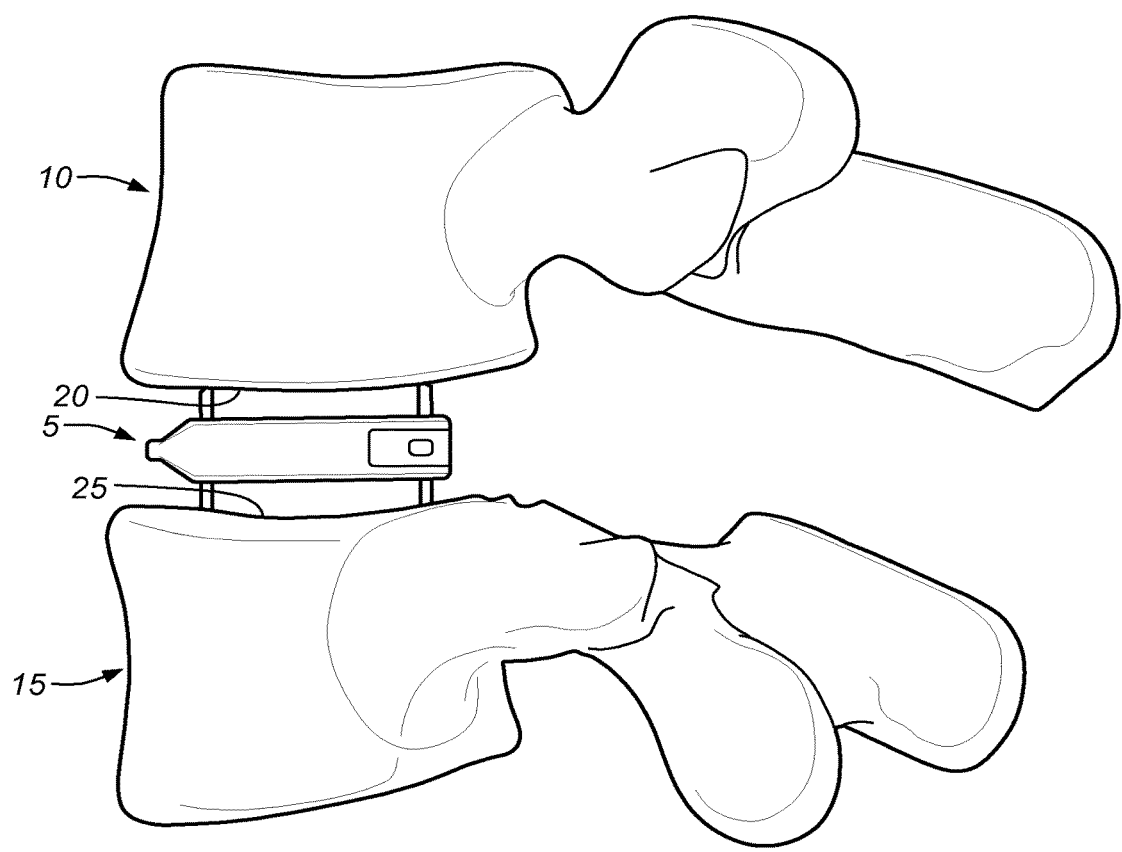
FIG. 1 depicts a schematic side view showing an expandable fusion device formed in accordance with the present invention, with the expandable fusion device being disposed between adjacent vertebral bodies.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112, paragraph six, interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

Figure 3:
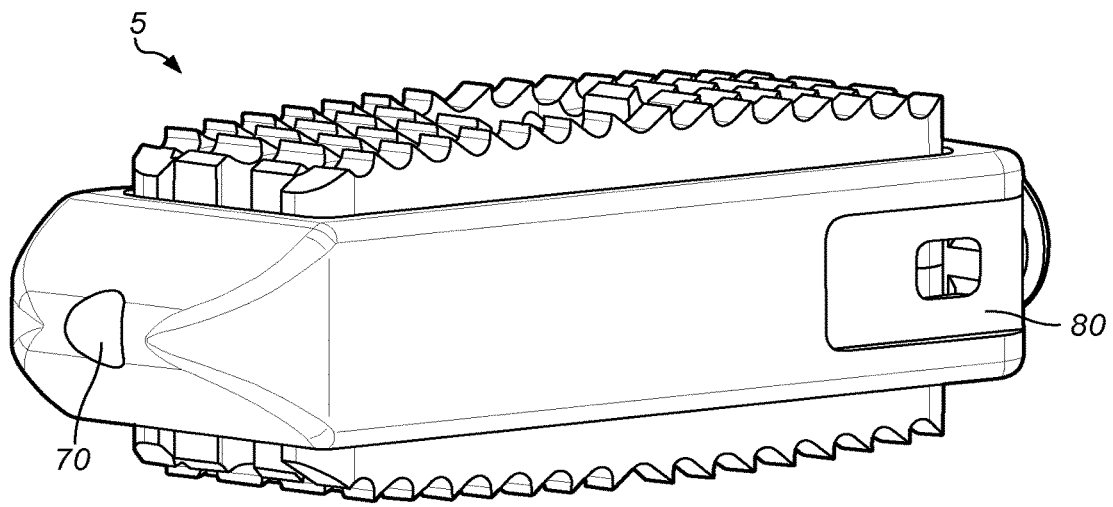
FIG. 3 depicts a schematic front perspective view of an expandable fusion device, with the expandable fusion device being shown in an unexpanded position.
Figure 4:
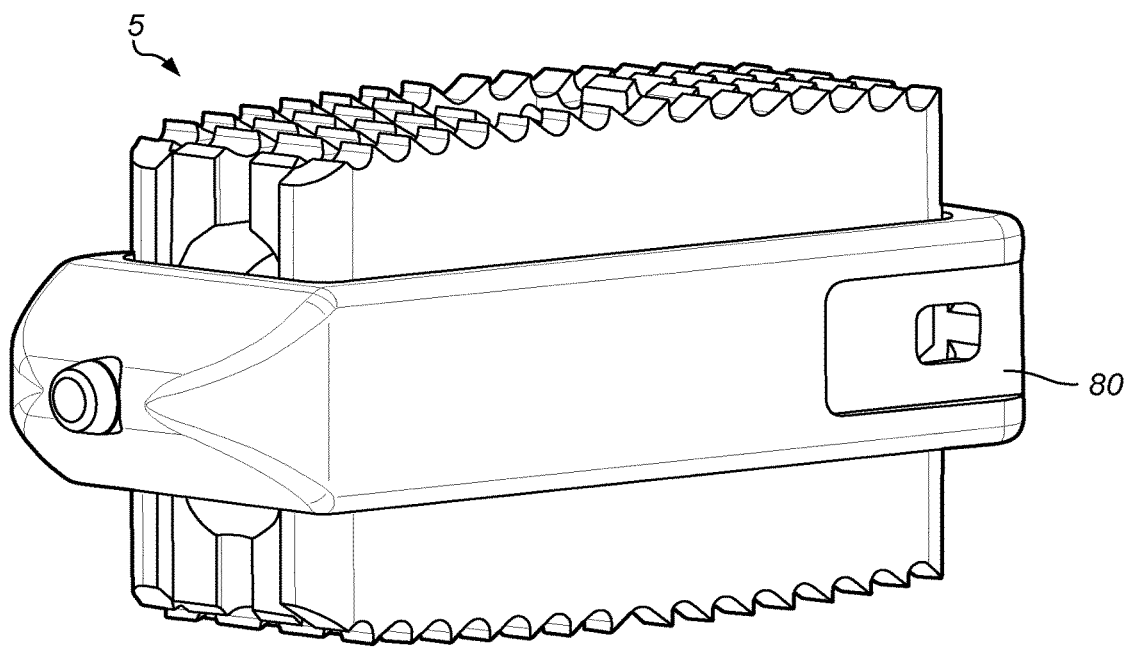
FIG. 4 depicts a schematic front perspective view of an expandable fusion device, with the expandable fusion device being shown in an expanded position.
Figure 5:
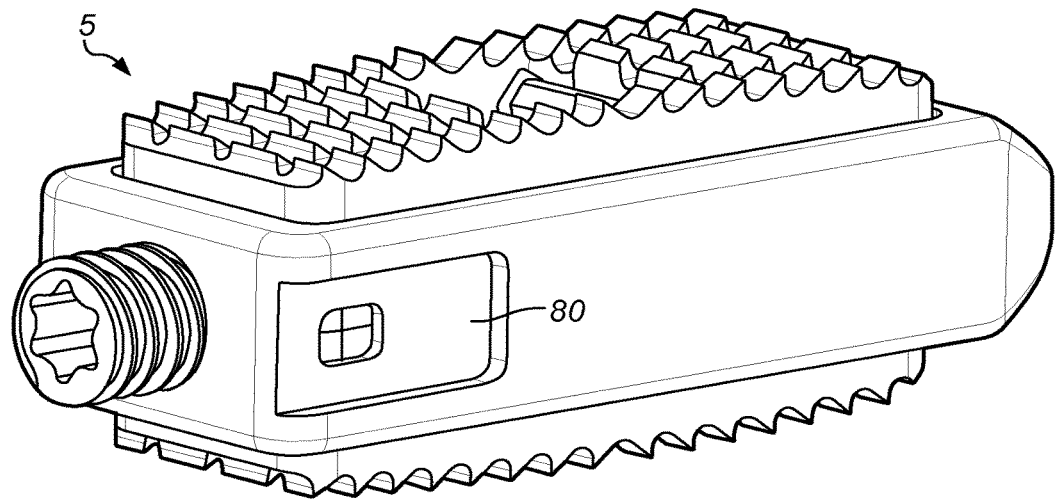
FIG. 5 depicts a schematic rear perspective view of an expandable fusion device, with the expandable fusion device being shown in an unexpanded position.
Figure 6:
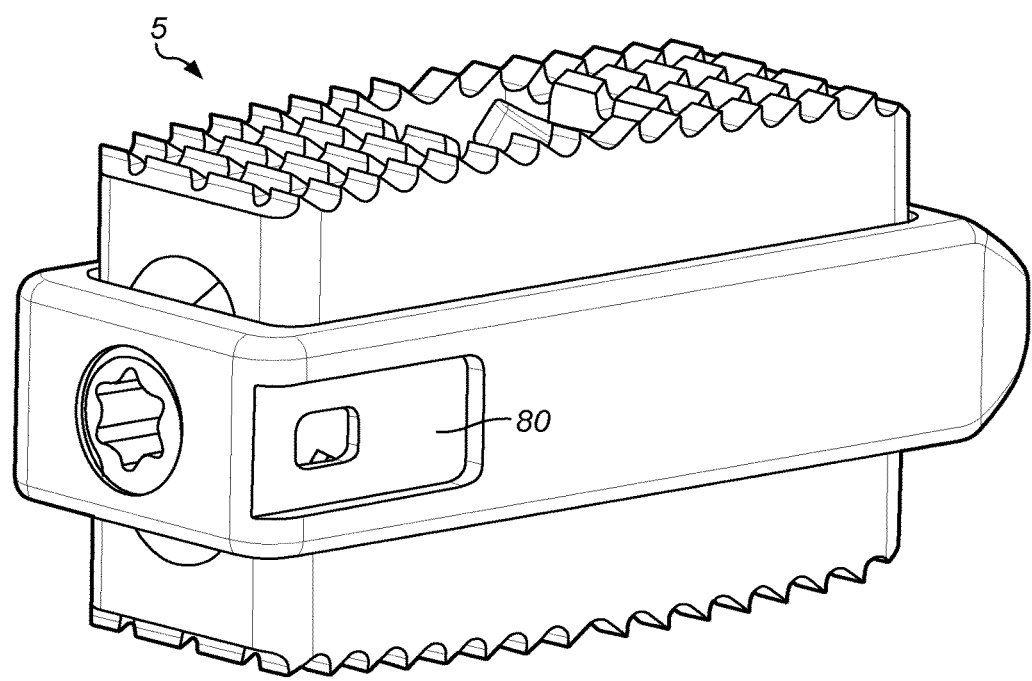
FIG. 6 depicts a schematic rear perspective view of an expandable fusion device, with the expandable fusion device being shown in an expanded position.

Looking first at FIG. 1, there is shown an intervertebral implant 5 (e.g., expandable fusion device) formed in accordance with the present invention, with the intervertebral implant 5 being shown disposed between a superior vertebral body 10 and an inferior vertebral body 15. As will hereinafter be discussed in further detail, intervertebral implant 5 may be inserted between superior vertebral body 10 and inferior vertebral body 15 while the intervertebral implant is in a contracted condition (e.g., as depicted in FIGS. 3 and 5), and thereafter expanded (e.g., as depicted in FIGS. 4 and 6) as necessary so as to span and engage the endplate 20 of superior vertebral body 10 and the endplate 25 of inferior vertebral body 15, whereby to support superior vertebral body 10 and inferior vertebral body 15 relative to one another.

Figure 2:
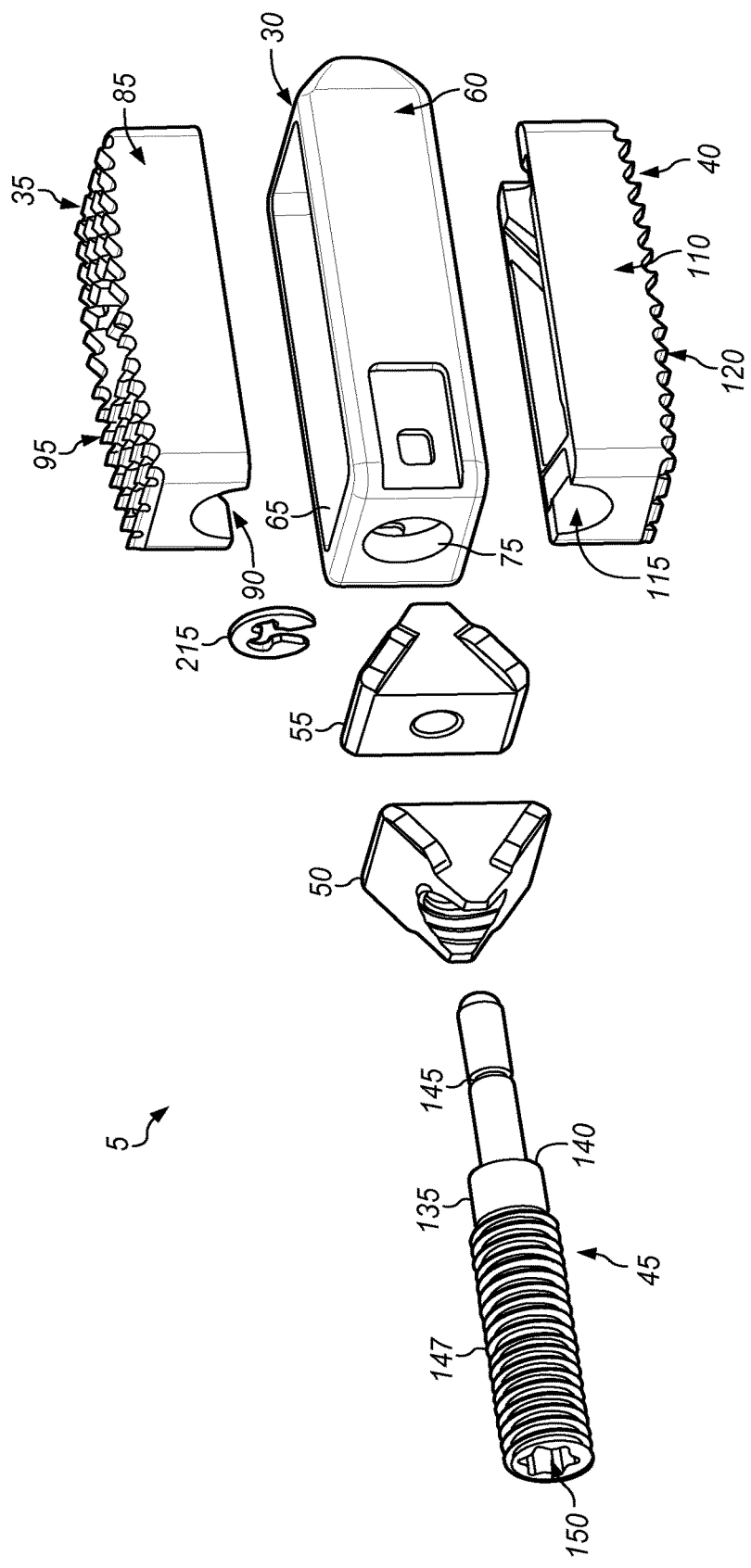
FIG. 2 depicts a schematic exploded view of an expandable fusion device.

In some embodiments, (e.g., as depicted in FIG. 2) intervertebral implant 5 (e.g., as depicted in FIG. 2) generally includes a cage 30, an upper body 35, a lower body 40, an expansion mechanism 45, a first expansion member 50 (e.g., positioned proximally) and a second expansion member 55 (e.g., positioned distally). As will hereinafter be discussed, the application of torque to expansion mechanism 45 in one direction causes first expansion member 50 and second expansion member 55 to separate, whereby to move upper body 35 and lower body 40 away from one another and hence increase the height of intervertebral implant 5. The application of torque to expansion mechanism 45 in the opposite direction causes first expansion member 50 and second expansion member 55 to draw towards one another, whereby to move upper body 35 and lower body 40 toward one another and hence decrease the height of intervertebral implant 5. In some embodiments, the mechanism may be reversed with, for example, the expansion members moving towards one another during expansion (although the opening for biological material might be reduced in such an embodiment).

Designs which may be similar but with for example expansion members conveying in the same direction may have a mechanical disadvantage relative to the embodiments described herein wherein the expansion members are conveyed in opposing directions. Expansion members which are conveyed in opposing directions may require half of the input torque to move as opposed to expansion members which are conveyed in the same direction.

In some embodiments, a cage 30 includes a generally rectangular structure 60 having a hollow interior 65, a distal opening 70 and a proximal opening 75. Two seats 80 are formed in the opposing side surfaces of cage 30.

Figure 15:
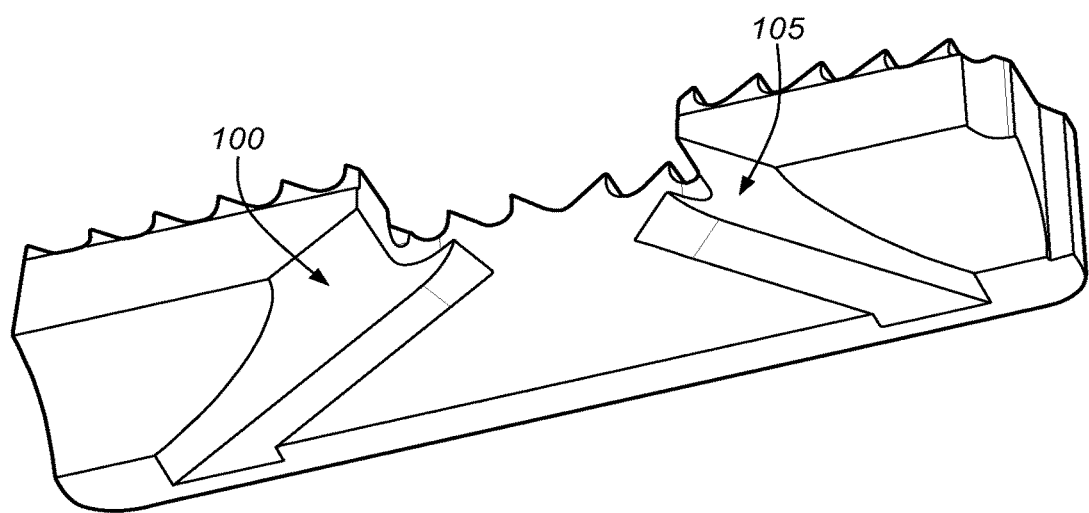
FIG. 15 depicts a schematic perspective cross-sectional view of an upper body.

Upper body 35 generally includes a block 85 having an inferior recess 90, and a textured superior surface 95, and a pair of inclined camming surfaces 100, 105. Camming surfaces 100, 105 of upper body 35 may be inclined in opposite directions (e.g., as depicted in FIG. 15).

Figure 13:
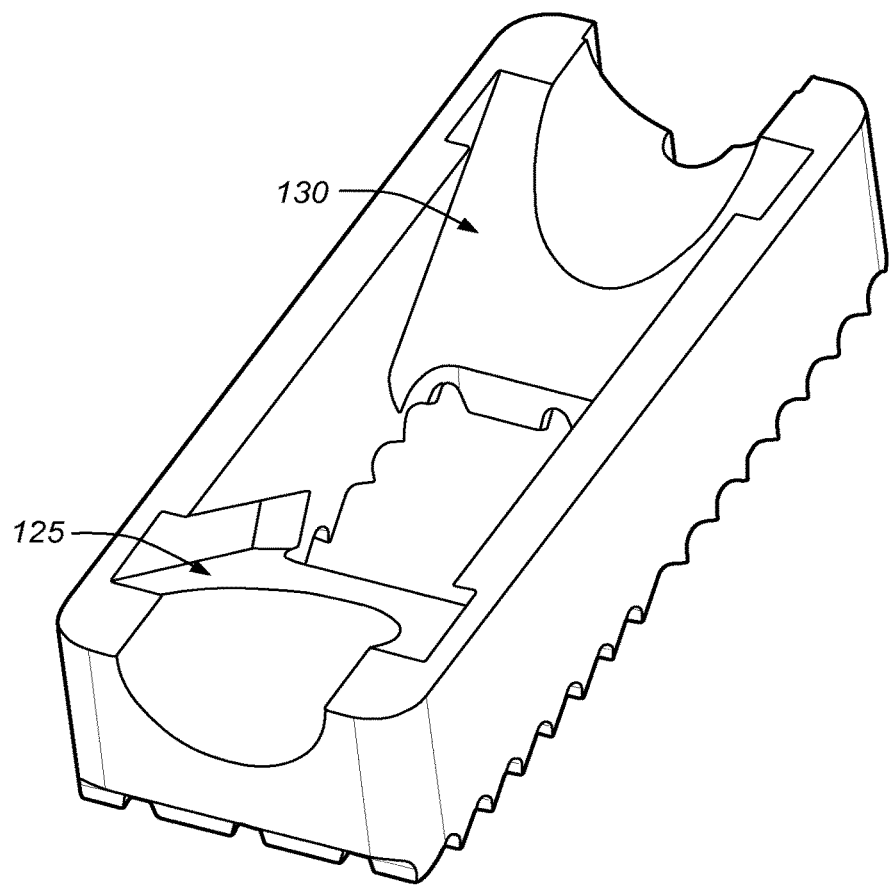
FIG. 13 depicts a schematic perspective view of a lower body.
Figure 14:
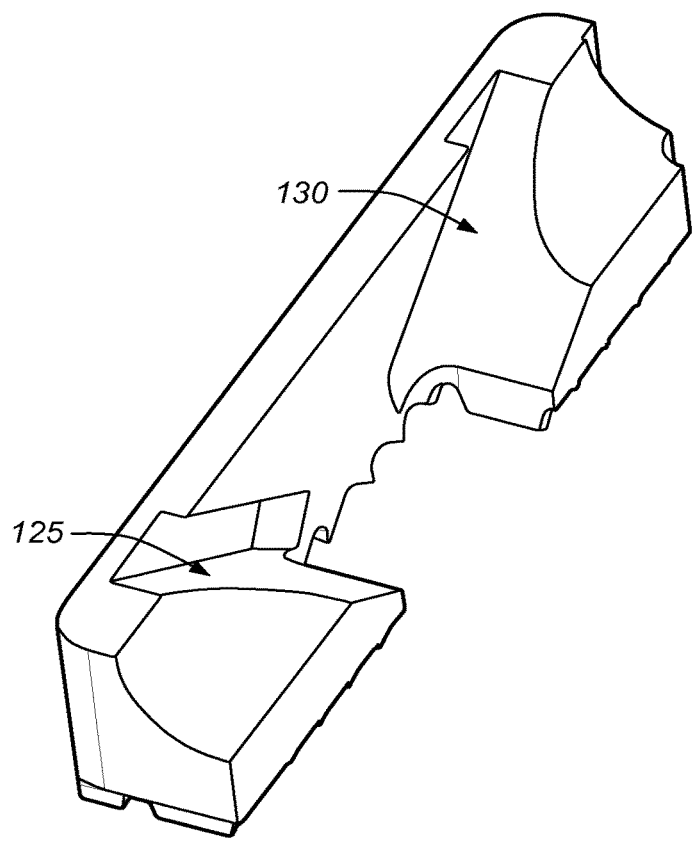
FIG. 14 depicts a schematic perspective cross-sectional view of a lower body.

Lower body 40 generally includes a block 110 having a superior recess 115, a textured inferior surface 120 and a pair of inclined camming surfaces 125, 130. Camming surfaces 125, 130 of lower body 40 may be inclined in opposite directions (e.g., as depicted in FIGS. 13-14).

In some embodiments, the camming surface 100 of upper body 35 and the camming surfaces 130 of lower body 40 extend parallel to one another, and the camming surfaces 105 of upper body 35 and the camming surface 125 of lower body 40 extend parallel to one another.

Expansion mechanism 45 generally includes an elongated shaft 135 having an annular shoulder 140 formed intermediate its length. A groove 145 is formed distal to annular shoulder 140. Screw threads 147 are formed on the outer surface of elongated shaft 135 proximal to annular shoulder 140. A noncircular bore 150 opens on the proximal end of expansion mechanism 45 and extends distally thereof.

Figure 7:
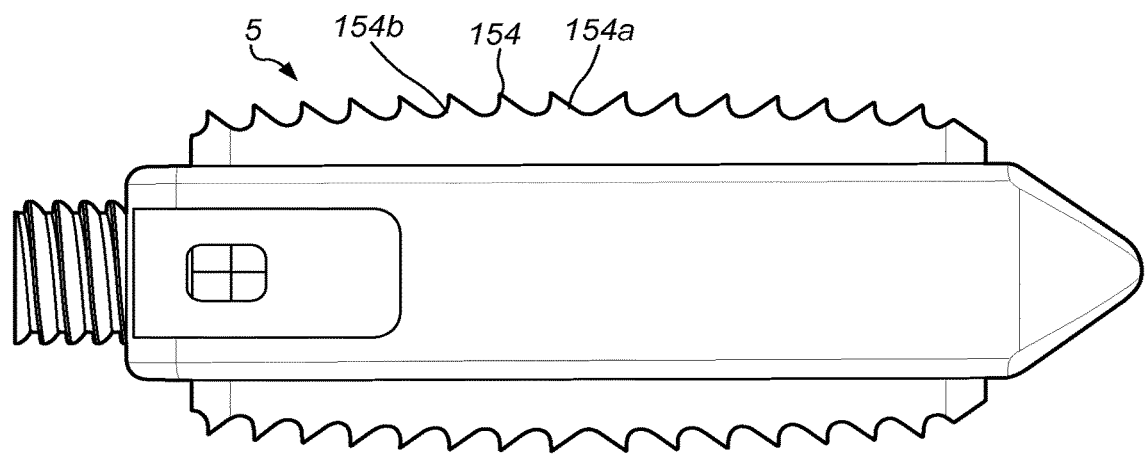
FIG. 7 is a schematic side view of an expandable fusion device, with the expandable fusion device being shown in an unexpanded position.

Superior and/or inferior surfaces of the implant (e.g., textured superior surface 95 and textured inferior surface 120) may include various features to facilitate engagement of the surfaces with endplates of adjacent vertebrae. In some embodiments, the implant may include a plurality of surface deformations positioned on the inferior surface and/or the superior surface. Surface deformations may include protrusions. For example (e.g., depicted in FIG. 7) superior surface of the implant 5 may include protrusions (e.g., teeth) 154 extending there from. During use, teeth 154 may extend/penetrate into adjacent boney structure of the upper and lower adjacent vertebrae. Such penetration may help to fix a position of the implant 5 relative to the vertebrae. Fixing or otherwise stabilizing the implant may reduce the likelihood of implant 5 being expelled from within the intervertebral space, and may promote bone attachment to and through implant 5. In some embodiments, various spray coatings may be applied to one or more exterior surfaces to, for example, enhance fixation with adjacent bone surfaces.

Figure 8:
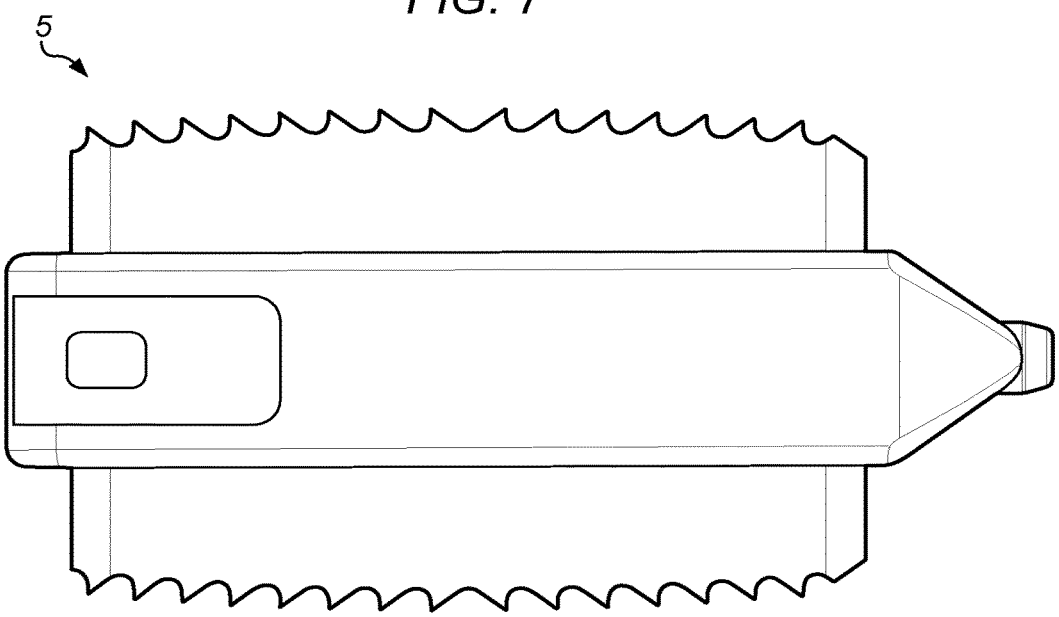
FIG. 8 depicts a schematic side view of an expandable fusion device, with the expandable fusion device being shown in an expanded position.
Figure 9:
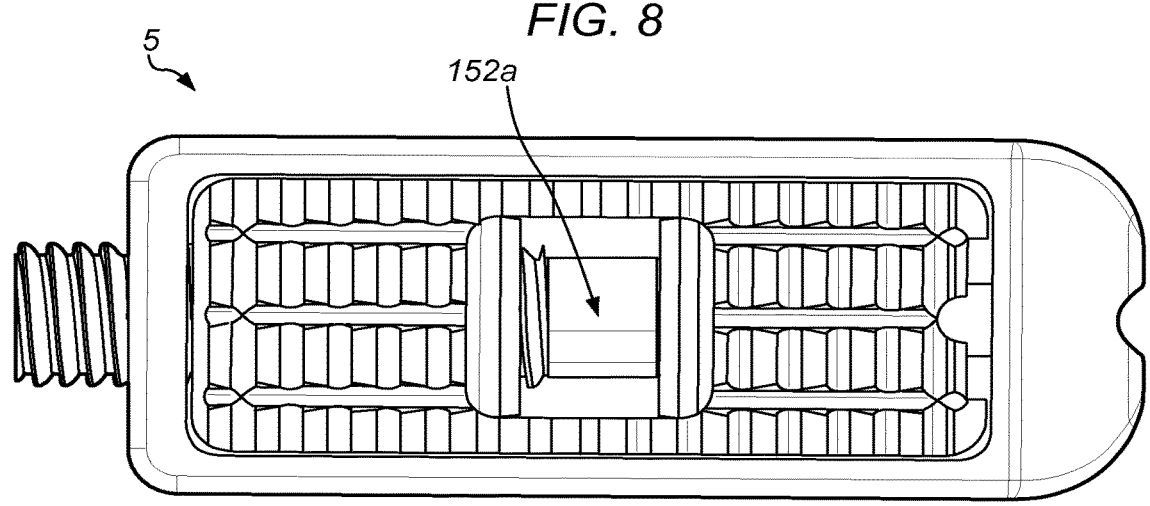
FIG. 9 depicts a schematic top view of an expandable fusion device.
Figure 10:
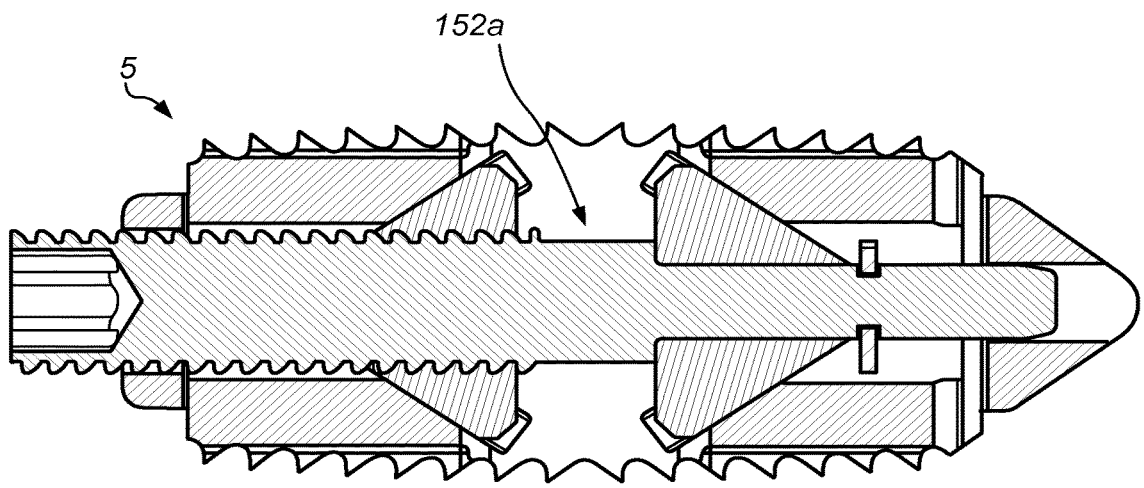
FIG. 10 depicts a schematic side cross-sectional view of an expandable fusion device, with the expandable fusion device being shown in an unexpanded position.
Figure 11:
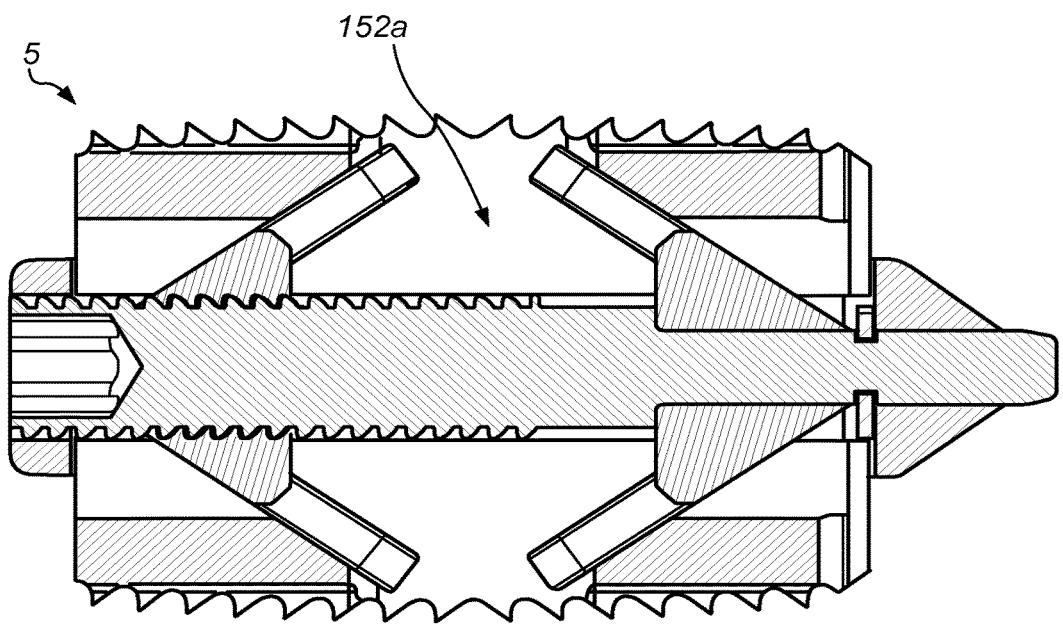
FIG. 11 depicts a schematic side cross-sectional view of an expandable fusion device, with the expandable fusion device being shown in an expanded position.
Figure 12:
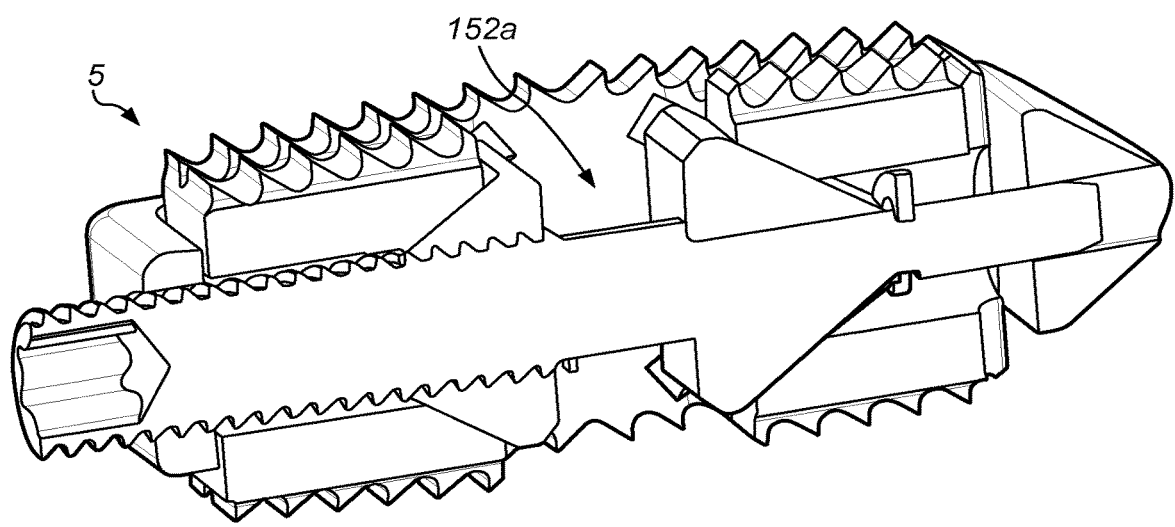
FIG. 12 depicts a schematic perspective cross-sectional view of an expandable fusion device, with the expandable fusion device being shown in an unexpanded condition.

In some embodiments, protrusions 154 may include directional teeth that facilitate movement of the members in a first direction, but inhibit movement of the members in a second opposing direction. For example, in the illustrated embodiment, teeth 154 include a ramped leading surface 154a and a substantially vertical trailing edge 154b (e.g., depicted in FIGS. 7-8). Thus, forward advancement of the members may be facilitated as boney structure of the vertebrae slides over ramped leading surface 154a of teeth 154 and backward advancement may be inhibited by substantially vertical trailing edge 154b hooking into or otherwise engaging the boney structure of the vertebrae.

In some embodiments, one or more portions of the implant may include one or more markers. Markers may be used to assess a position of one or more portions of the implant during implantation in a subject. A portion of the implant may include none, one or multiple markers. Markers may provide radiographic opacity. Markers may be biocompatible. Markers may be of any size or shape. In some embodiments, a system may have multiple markers with different shapes in order to more easily identify different portions or directions of the system and/or an orientation of one or more portions of the implant. In some embodiments, one or more markers may be formed from gold or tantalum.

In some embodiments, the implant 5 may include an opening 152a extending through the implant (e.g., depicted in FIGS. 9-12). The opening may hold biological material during use. In some embodiments, opening 152a may be filled with a substance/material to facilitate bone growth/fusion. Once implant 5 is implanted, the opening may facilitate a column of bone growth between the adjacent vertebrae through the opening 152a. In some embodiments, an opening (e.g., opening 152a) may function as a graft window containing bone chips and/or materials which facilitate tissue (e.g., bone) growth. The opening may increase in size as the first and second expansion members move away from each other as the implant is deployed.

Figure 20:
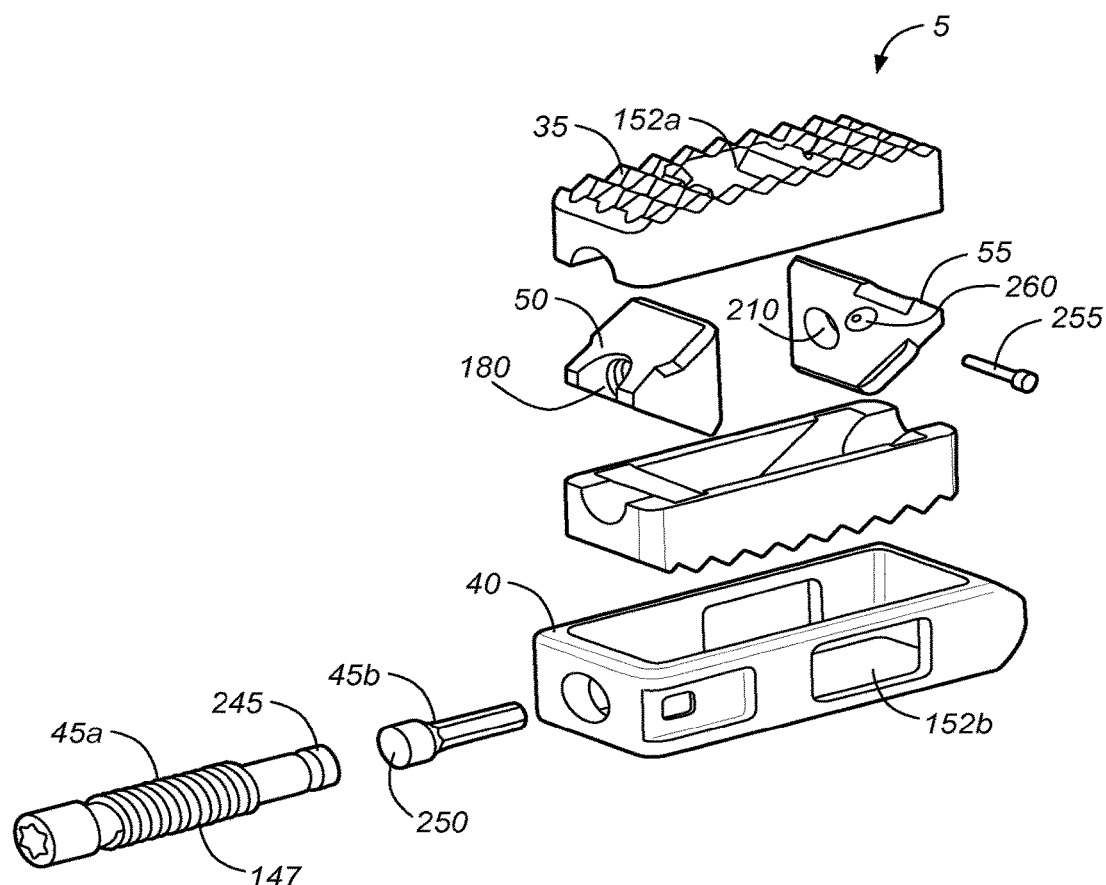
FIG. 20 depicts a schematic exploded view of an expandable fusion device.

In some embodiments, implant 5 may include one or more second openings 152b (e.g., depicted in FIG. 20). The second openings may be positioned on either side of cage 30. The openings may facilitate insertion of biological material. After positioning an implant during use opening 152a may be blocked by the vertebrae and therefore additional openings 152b may facilitate in packing of biological material (e.g., bone graft). The openings may be initially at least partially blocked by the first and second expansion members and/or the upper and lower bodies, as the implant is expanded the second openings may open up.

Figure 29:
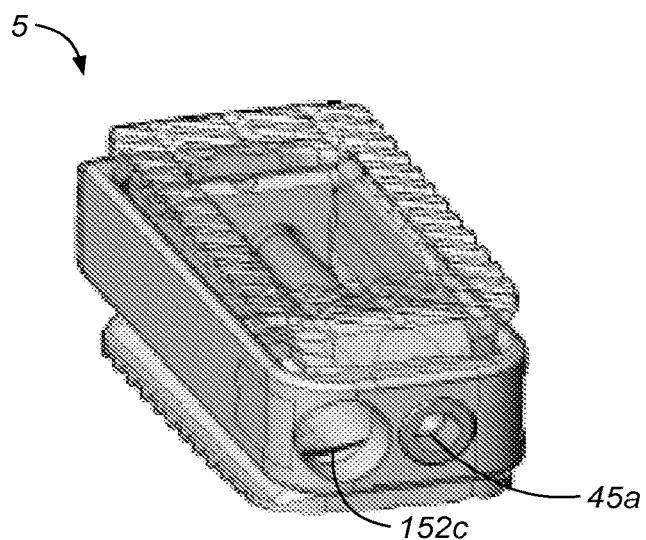
FIG. 29 depicts a schematic perspective view of an expandable fusion implant in an expanded state wherein an upper body portion of the implant is depicted as transparent.
Figure 30:
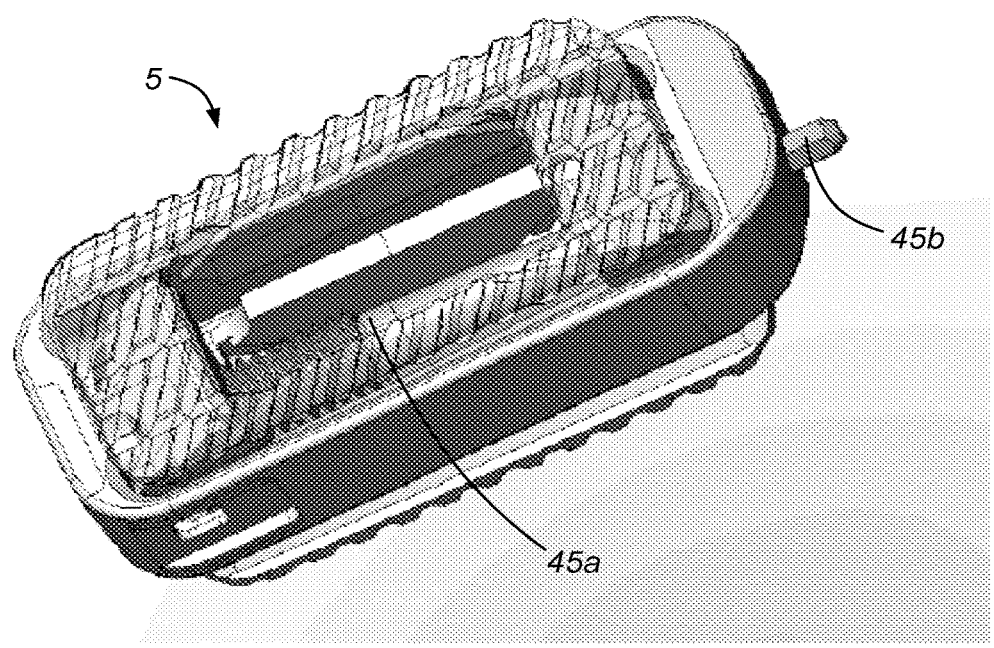
FIG. 30 depicts a schematic perspective view of an expandable fusion implant in an expanded state wherein an upper body portion of the implant is depicted as transparent.
Figure 31:
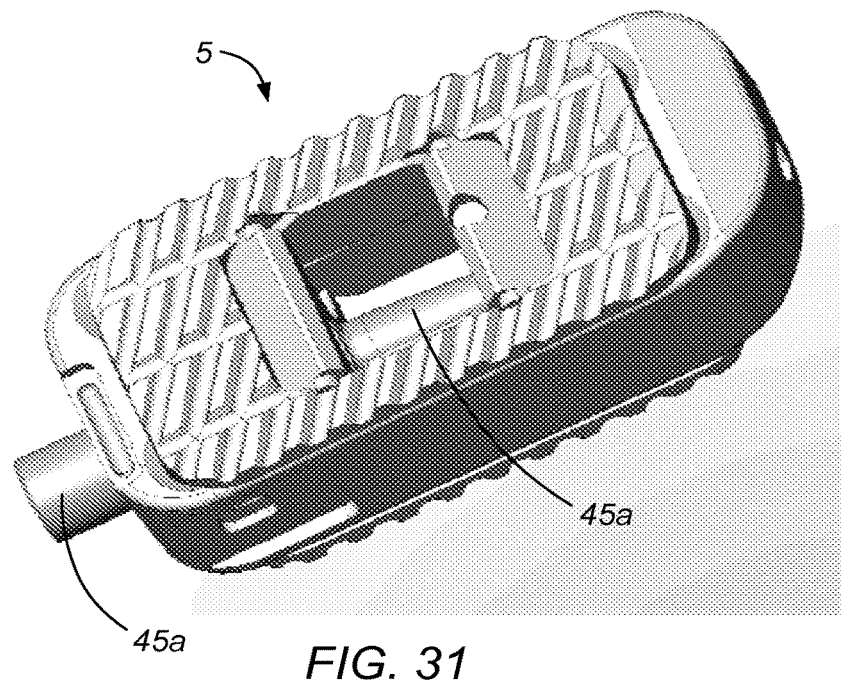
FIG. 31 depicts a schematic perspective view of an expandable fusion implant in a contracted state.
Figure 32:
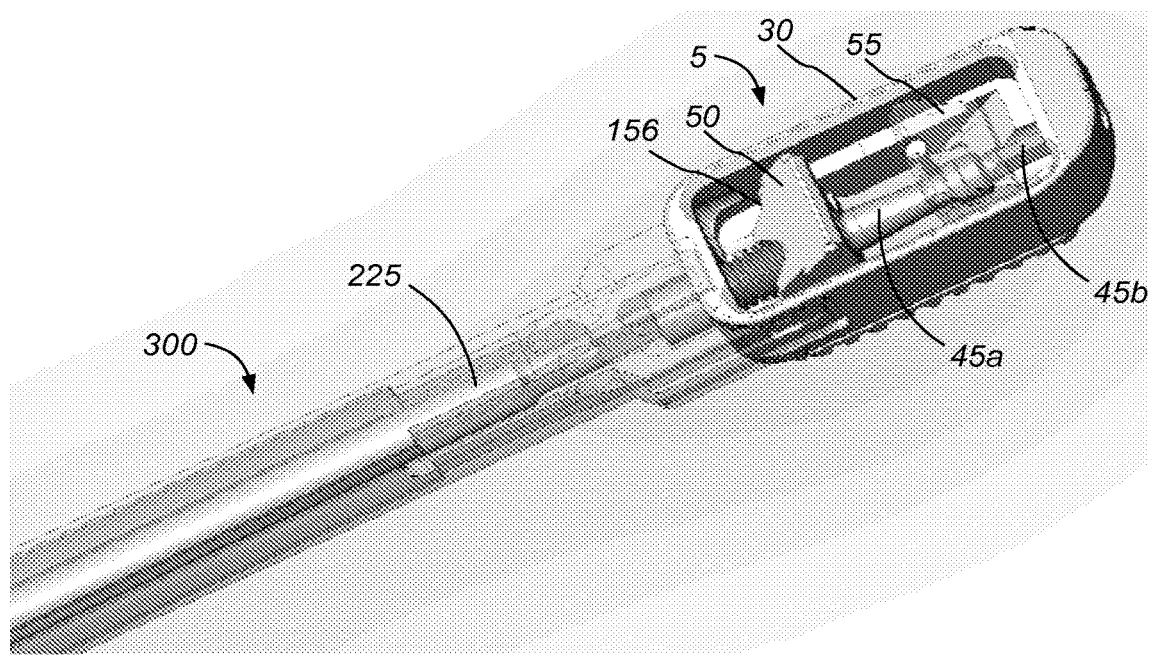
FIG. 32 depicts a schematic perspective view of an expandable fusion implant in a contracted state coupled to an insertion instrument with portions of the insertion instruments depicted as transparent. An upper body of the implant is not depicted and a second expandable member is depicted as transparent.
Figure 33:
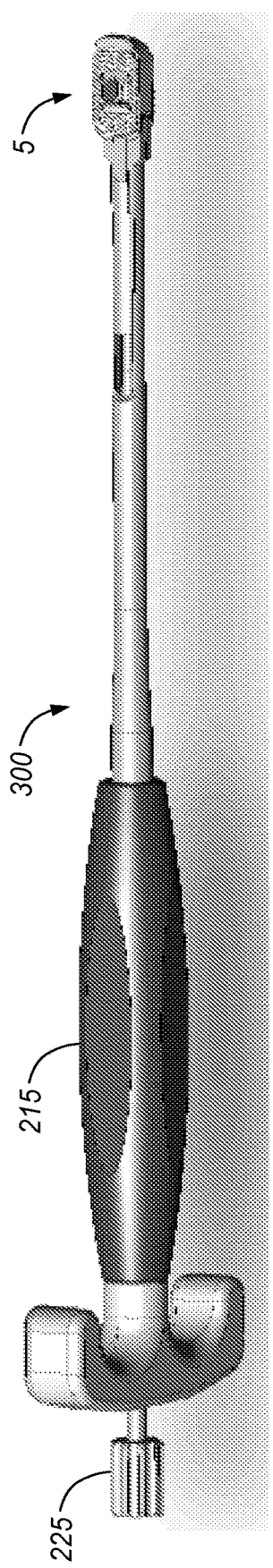
FIG. 33 depicts a schematic view of an insertion instrument with an expandable fusion device.
Figure 34:
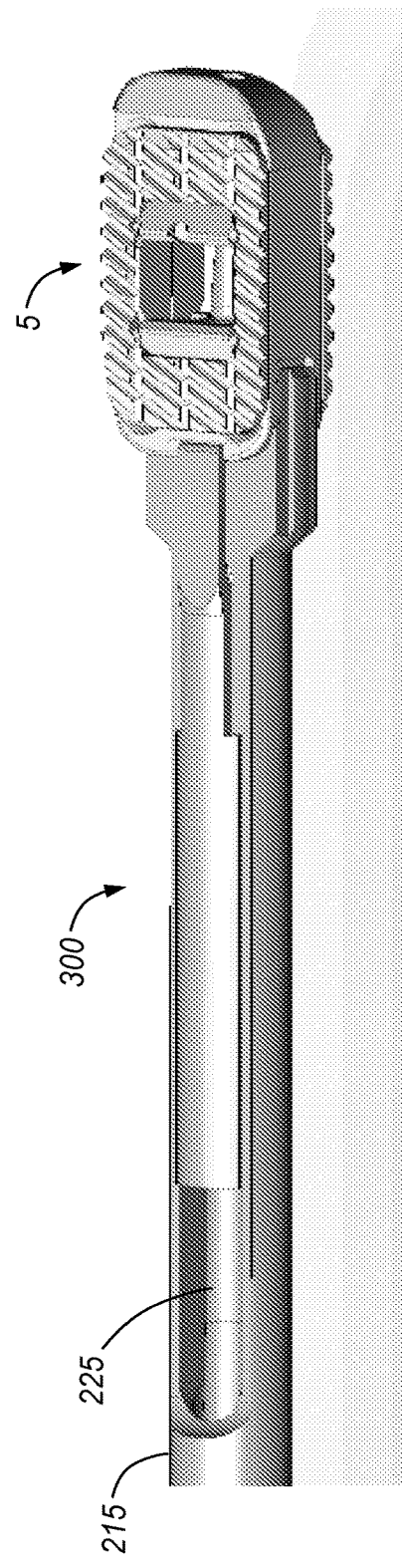
FIG. 34 depicts a schematic view of a distal end of an insertion instrument with an expandable fusion device.
Figure 35:
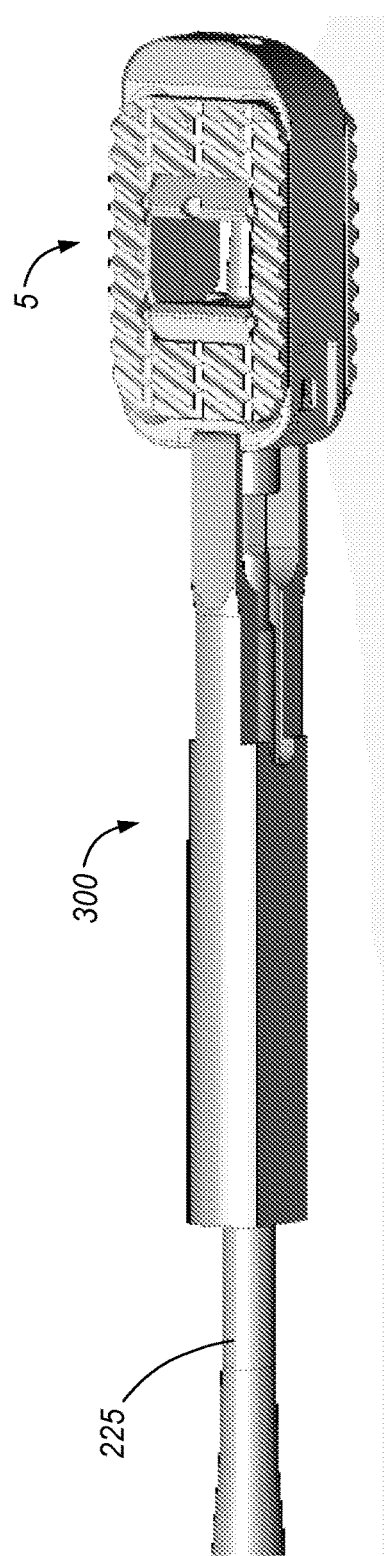
FIG. 35 depicts a schematic view of a distal end of an insertion instrument with an expandable fusion device with a portion of the insertion instrument removed for clarity.
Figure 36:
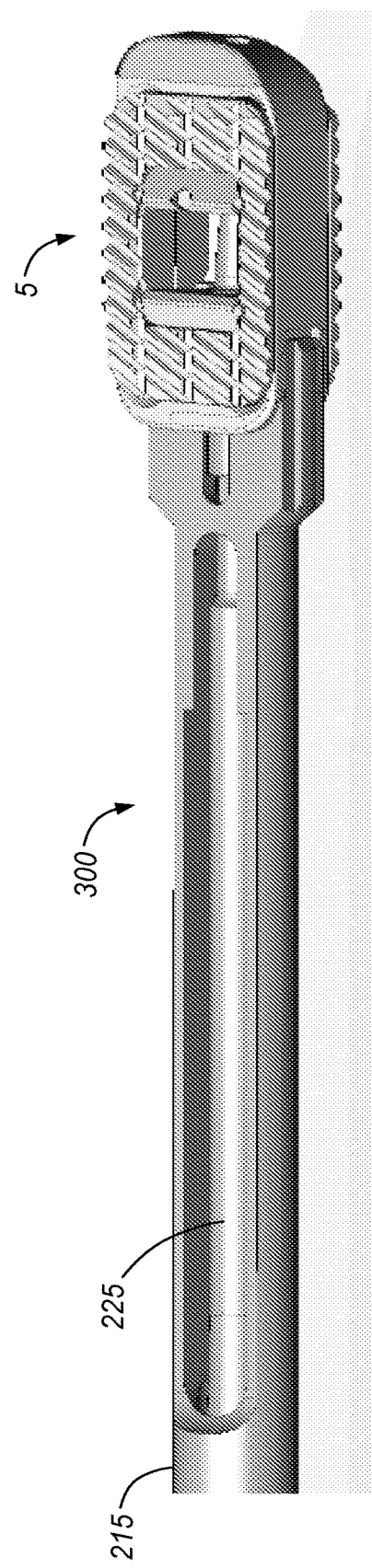
FIG. 36 depicts a schematic view of a distal end of an insertion instrument with an expandable fusion device with a portion of the insertion instrument removed for clarity.
Figure 37:
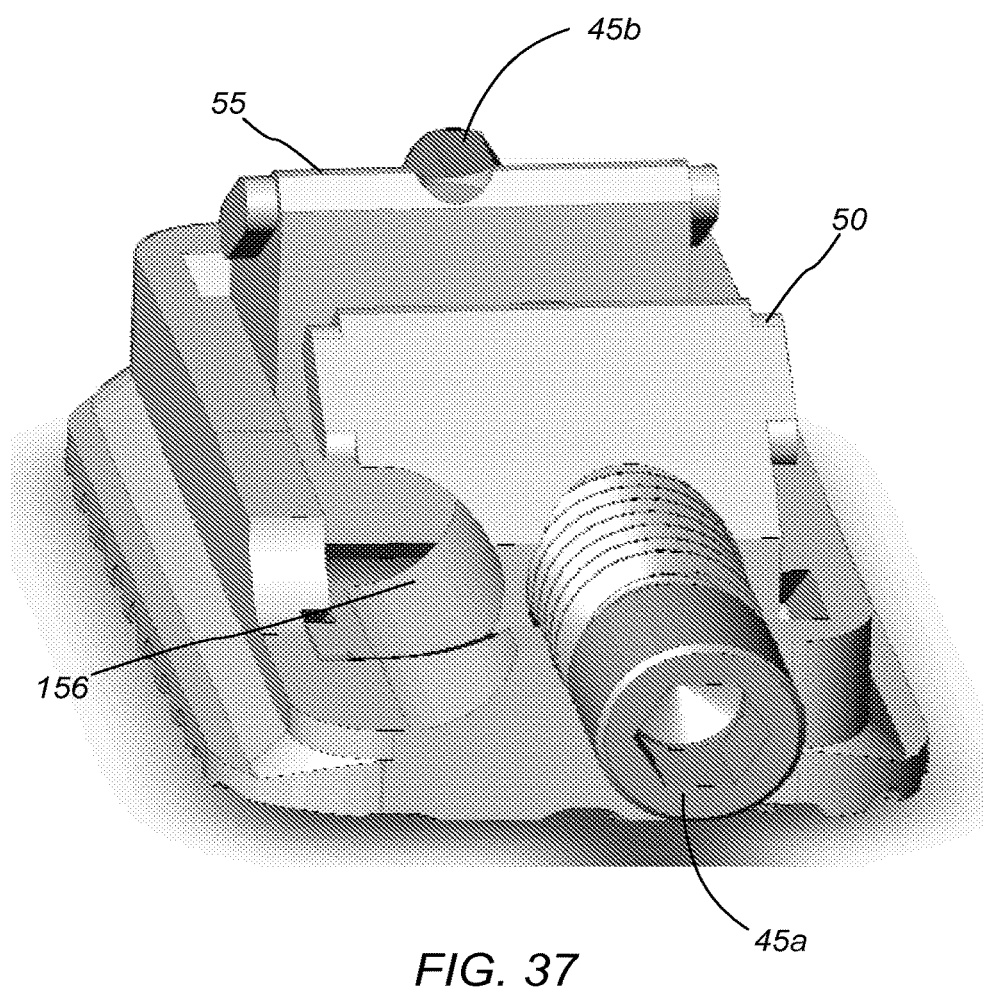
FIG. 37 depicts a schematic perspective view of an expandable fusion implant in a contracted state. At least an upper body and a cage of the implant is not depicted.

In some embodiments, implant 5 may include a proximal opening 152c (e.g., depicted in FIG. 29). A proximal opening may allow biological material to be positioned in the interior of the implant after the implant has been positioned. The proximal opening may facilitate insertion of biological material after insertion of the implant. In some embodiments, a proximal opening in the implant may necessitate positioning the expansion mechanism (e.g., elongated members 45a-b as depicted in FIGS. 30-31) off center in order to allow for creating a large enough proximal opening. In some embodiments, the first expansion member 50 may be modified to allow biological material inserted through the proximal opening to pass beyond the first expansion member into the space between the first and the second expansion member 50, 55. The first expansion member may include an opening 156 and/or shaped to create an opening in combination with an interior surface of the cage 30 (e.g., as depicted in FIGS. 32 and 37).

Figure 19:
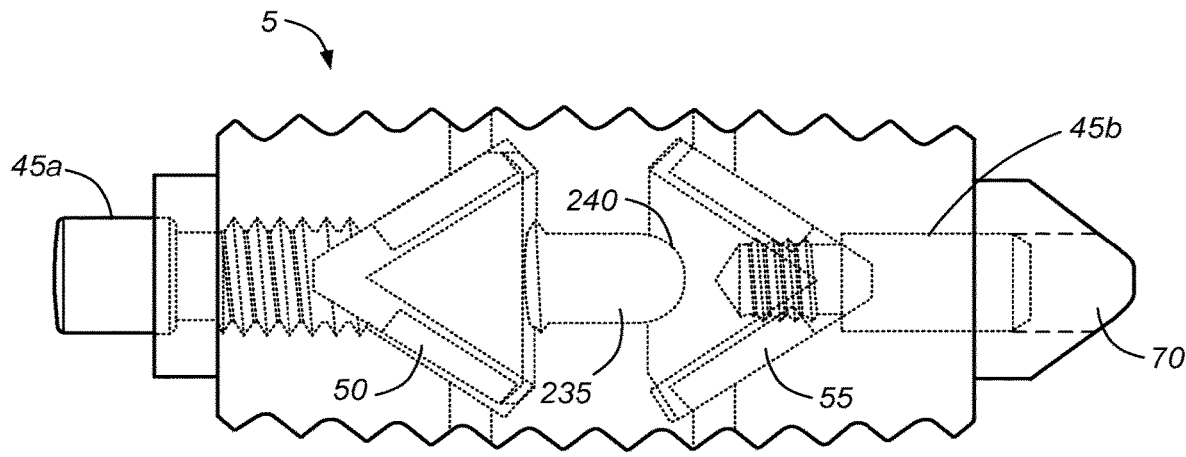
FIG. 19 depicts a schematic transparent side view of an expandable fusion device.

In some embodiments, a distal end 235 of the elongated member (e.g., expansion mechanism 45a) engages, during use, a proximal end of the second expansion member 55. In such an embodiment, the distal end of the elongated member abuts a proximal end of the second expansion member as opposed to extending through an opening in the second expansion member. The distal end may engage a recess 240 in the second expansion member 55 (e.g., as depicted in FIG. 19). A recess may include a shallow opening. The distal end may turn freely in the recess. The recess may assist in centering and/or positioning the distal end of the elongated member 45 such that the distal end is inhibited from misaligning and/or disengaging from the second expansion member. In some embodiments, the implant 5 may include a second elongated member 45b. The second elongated member 45b may be positioned in the second expansion member 55 and opening 70 such that the second elongated member keeps the second expansion member centered.

In some embodiments, the expansion mechanism may include a first elongated member 45a and a second elongated member 45b (e.g., as depicted in FIG. 20). The first elongated member 45a may include a proximally threaded portion 147. The first expansion member 50 may include a threaded opening 180 which the threaded portion of the first elongated member engages, during use. The second elongated member 45b may be positionable, during use, in an opening 210 in the second expansion member 55. A distal end 245 of the first elongated member 45a may engage, during use, a proximal end 250 of the second elongated member 45b. In some embodiments, a distal end of the first elongated member may engage, during use, a proximal end of the second elongated member such that the distal end of the first elongated member is positioned in the opening in the second expansion member. The distal end of the first elongated member may turn freely in the opening in the second expansion member. In some embodiments, the second elongated member may function to keep the second expansion member 55 central in the body of the implant. In some embodiments, the second elongated member may be essentially non-rotating relative to the first elongated member.

The result is that the separation between the expansion members is thus equal to just one pitch of the thread per rotation, or ½ pitch of movement relative to the endplate (upper & lower body) each. As such for a given torque one may provide approximately twice the lifting force as compared to dual expansion members moving in the same direction at 1 pitch per rotation. Embodiments discussed herein would have twice the separation force relative to a turnbuckle thread configured with opposing expansion members (or even with expansion members moving in the same direction) because they separate/collapse at a rate of 2 pitches per rotation and thus have twice the motion relative to the endplates.

In some embodiments, a size of the expansion member (e.g., screw) may be reduced to get the same force at a lower torque because passive rotation within one of the expansion members is more efficient. One may reduce the angle of the ramp or have a single ramp, but you would need considerably more travel to achieve the same height and would run into length limitations. Many embodiments described herein increase rotations not travel.

Forming the expansion mechanism from two elongated members as opposed to a single elongated member has several advantages. For example when retracting upper body 35 and lower body 40 from an engaged position to an unengaged position, torque applied to the expansion mechanism during retraction may lead to failure of the expansion mechanism when the expansion mechanism includes a single elongated member. When the expansion mechanism includes two elongated members, failure of the expansion mechanism when counter (retracting) torque is applied is inhibited.

In some embodiments, one or more of the expansion members may include a locking member 255. The locking member may be positionable in the second expansion member 55 such that the second elongated member is inhibited, during use, from removal from the opening in the second expansion member. The locking member may include a pin.

The pin may be positioned in an opening in the second expansion member. In some embodiments, the locking member may engage a recess 260 in the second elongated member. The recess may circumscribe the circumference of the second elongated member such that the second elongated member does not have to be oriented in a particular direction relative to the second elongated member. In some embodiments, the locking member may be used in combination with the single elongated member (e.g., snap ring 215 as depicted in FIG. 2).

Figure 16:
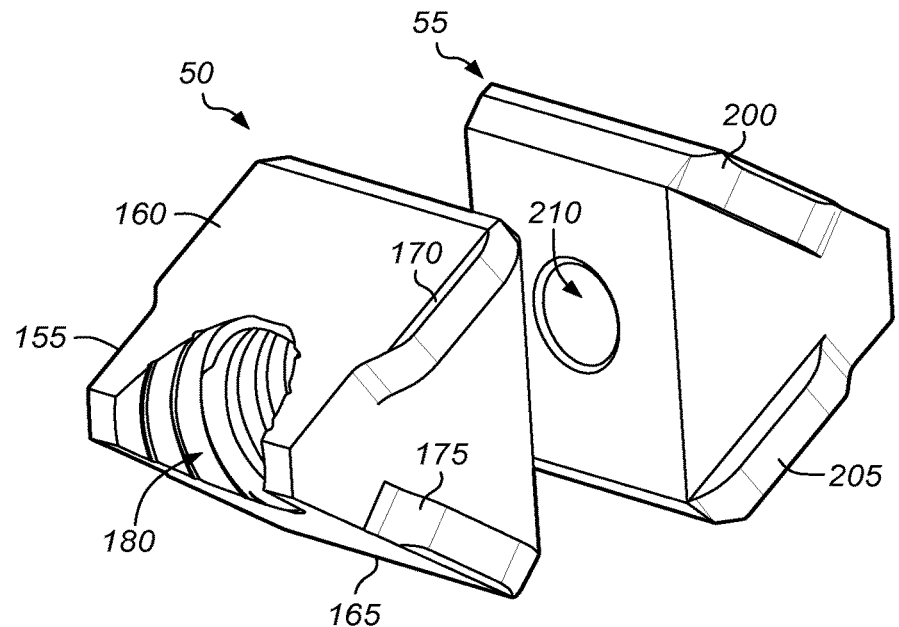
FIG. 16 depicts a schematic right side perspective view of the proximal and second expansion members.

In some embodiments, first expansion member 50 includes a generally wedge-shaped body 155 having a superior camming surface 160, an inferior cam surface 165, a pair of superior fingers 170 and a pair of inferior fingers 175 (e.g., as depicted in FIG. 16). Significantly, superior camming surface 160 of first expansion member 50 extends parallel to camming surface 100 of upper body 35, and inferior camming surface 165 of first expansion member 50 extends parallel to camming surface 125 of lower body 40. In lordotic embodiments these surfaces may only be parallel in the open position. They are not parallel when closed. First expansion member 50 may include a threaded bore 180 extending there through. Threaded bore 180 is sized to be threadingly engaged by screw threads 147 on elongated shaft 135.

Figure 17:
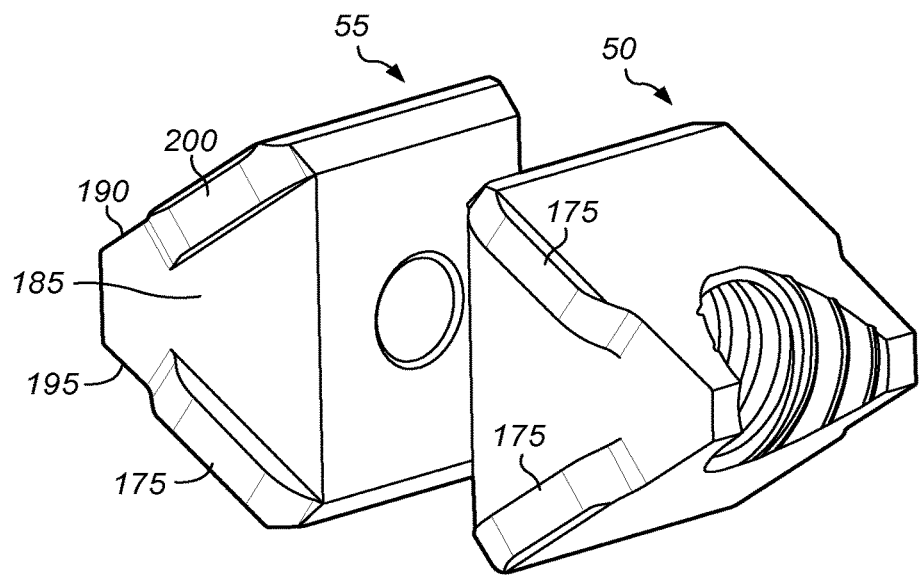
FIG. 17 depicts a schematic left side perspective view of the proximal and second expansion members.

In some embodiments, second expansion member 55 includes a generally wedge-shaped body 185 having a superior camming surface 190, an inferior camming surface 195, a pair of superior fingers 200 and a pair of inferior fingers 205 (e.g., as depicted in FIGS. 16-17). Significantly, superior camming surface 190 of second expansion member 55 extends parallel to camming surface 105 of upper body 35, and inferior camming surface 195 of second expansion member 55 extends parallel to camming surface 130 of lower body 40. In lordotic embodiments these surfaces may only be parallel in the open position. They are not parallel when closed. Second expansion member 55 may include a smooth bore 210 extending there through. Smooth bore 210 may be sized to receive the portion of expansion mechanism 45 distal to annular shoulder 140.

Camming surfaces of the upper/lower bodies and the expansion members may be substantially flat as depicted in some of the attached FIGS. In some embodiments, at least some of the camming surfaces may be curved. Complementary camming surfaces may be complementarily shaped. Complementary camming surfaces may not be complementarily shaped.

In some embodiments, intervertebral implant 5 may be assembled so that expansion mechanism 45 extends through proximal opening 75 in cage 30 (without engaging proximal opening 75 in cage 30), and first expansion member 50 and second expansion member 55 are disposed on shaft 135 of expansion mechanism 45 within the hollow interior 65 of cage 30. More particularly, first expansion member 50 may be mounted on elongated shaft 135 of expansion mechanism 45 so that screw threads 147 are threadingly received in threaded bore 180 of first expansion member 50, and second expansion member 55 is mounted on elongated shaft 135 of expansion mechanism 45 so that second expansion member 55 is captured on elongated shaft 135 between annular shoulder 140 and a snap ring 215 secured in groove 145. At the same time, upper body 35 and lower body 40 may extend into hollow interior 65 of exterior body 30 so that (i) camming surface 100 of upper body 35 rides on camming surface 160 of first expansion member 50, (ii) camming surface 105 of upper body 35 rides on camming surface 190 of second expansion member 55, (iii) camming surface 125 of lower body 40 rides on camming surface 165 of first expansion member 50, and (iv) camming surface 130 of lower body 40 rides on camming surface 195 of second expansion member 55.

It will be appreciated that, as a result of the foregoing construction, the application of torque to expansion mechanism 45 in one direction (e.g., in a noncircular bore 150 in expansion mechanism 45) causes first expansion member 50 and second expansion member 55 to separate, whereby to move upper body 35 and lower body 40 apart and hence increase the height of intervertebral implant 5. It will be appreciated that, as a result of the foregoing construction, the application of torque to expansion mechanism 45 in the opposite direction causes first expansion member 50 and second expansion member 55 to draw together, whereby to move upper body 35 and lower body 40 together and hence decrease the height of intervertebral implant 5.

Figure 21:
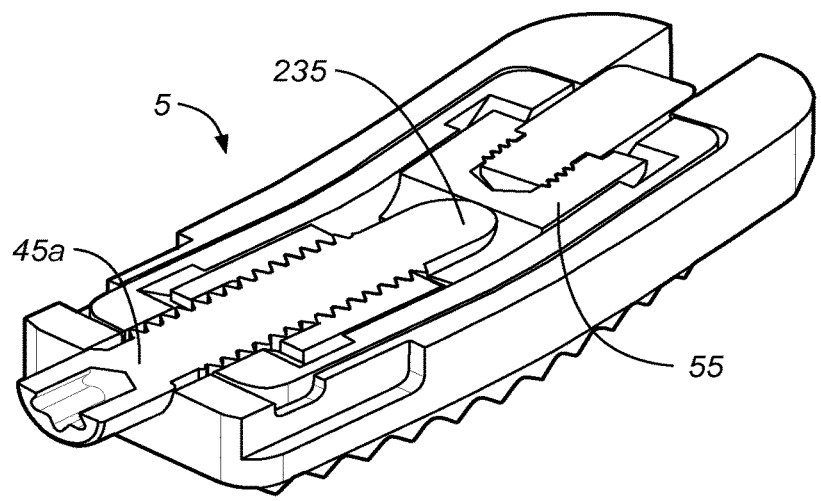
FIG. 21 depicts a schematic cross-sectional view of a curved expandable fusion device in an unexpanded state.
Figure 22:
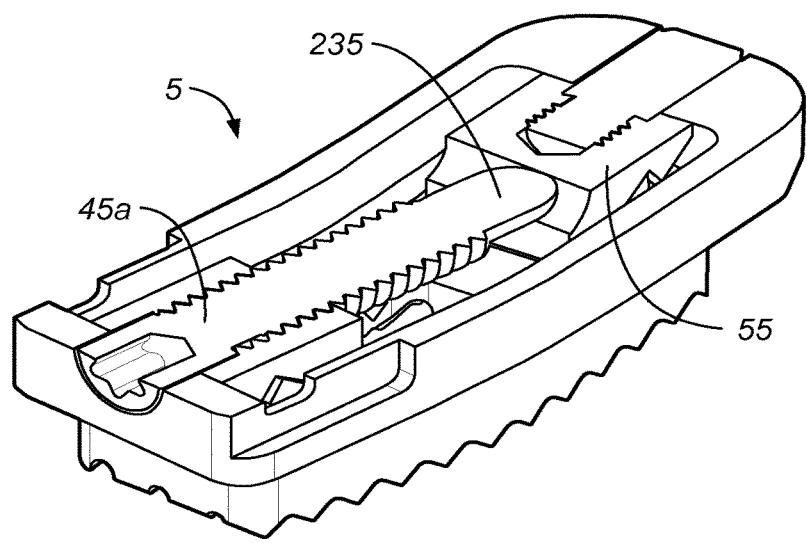
FIG. 22 depicts a schematic cross-sectional view of a curved expandable fusion device in an expanded state.

In some embodiments, the intervertebral implant 5 may include a curved cross-section. Straight designs are more commonly associated with PLIF (direct posterior placement in pairs), or lateral approaches (one longer device placed from the side of the spine). FIG. 21 is a schematic cross-sectional view of a curved expandable fusion device in an unexpanded state with a curved cross-section. FIG. 22 is a schematic cross-sectional view of a curved expandable fusion device in an expanded state with a curved cross-section. In some embodiments, portions of the implant may be curved or angled in order to accommodate the curved cross-section of the perimeter. In some embodiments, expansion members and the expansion mechanism may not require adjustments to assimilate into an implant with a curved perimeter. The distal end 235 of the expansion mechanism 45a may engage a recess 240 in the second expansion member 55 as discussed herein and in the case of a curved implant the recess may adjusted to compensate for the varying angle of engagement of the distal end with the recess during expansion. In some embodiments, the distal end of the expansion mechanism may be curved in order to accommodate a curved perimeter.

Figure 23:
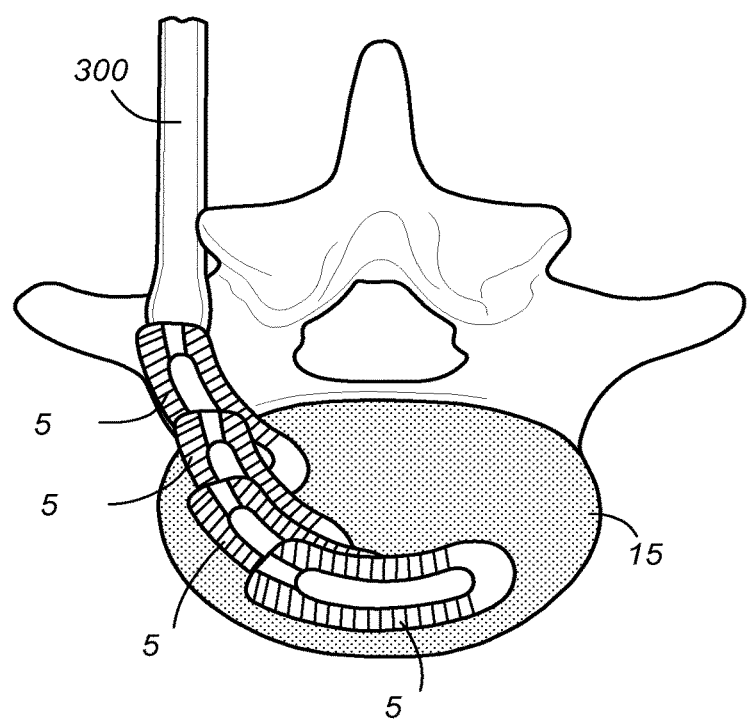
FIG. 23 depicts a schematic view of a curved expandable fusion device as the device is being inserted between two adjacent vertebrae.

The reason TLIF cages are typically curved is that the surgical technique would be to place them from a posterior-lateral approach, as much as 45 degrees off the midline, where they are tamped and rotated to the front of the vertebral body. A curved implant may facilitate insertion of the implant between adjacent vertebrae. An implant with a curved perimeter may better mimic and accommodate the existing perimeter of the average vertebra. FIG. 23 depicts a schematic view of a curved expandable fusion device 5 as the device is being inserted between two adjacent vertebrae. In some embodiments, the implant inserter may be curved. The expansion mechanism may have a flexible shaft to allow rotation within the curve. The relative advantages of an expandable feature may in fact be greater because it would significantly reduce the impaction required to maneuver the device into final position at the front of the spine.

Figure 18:
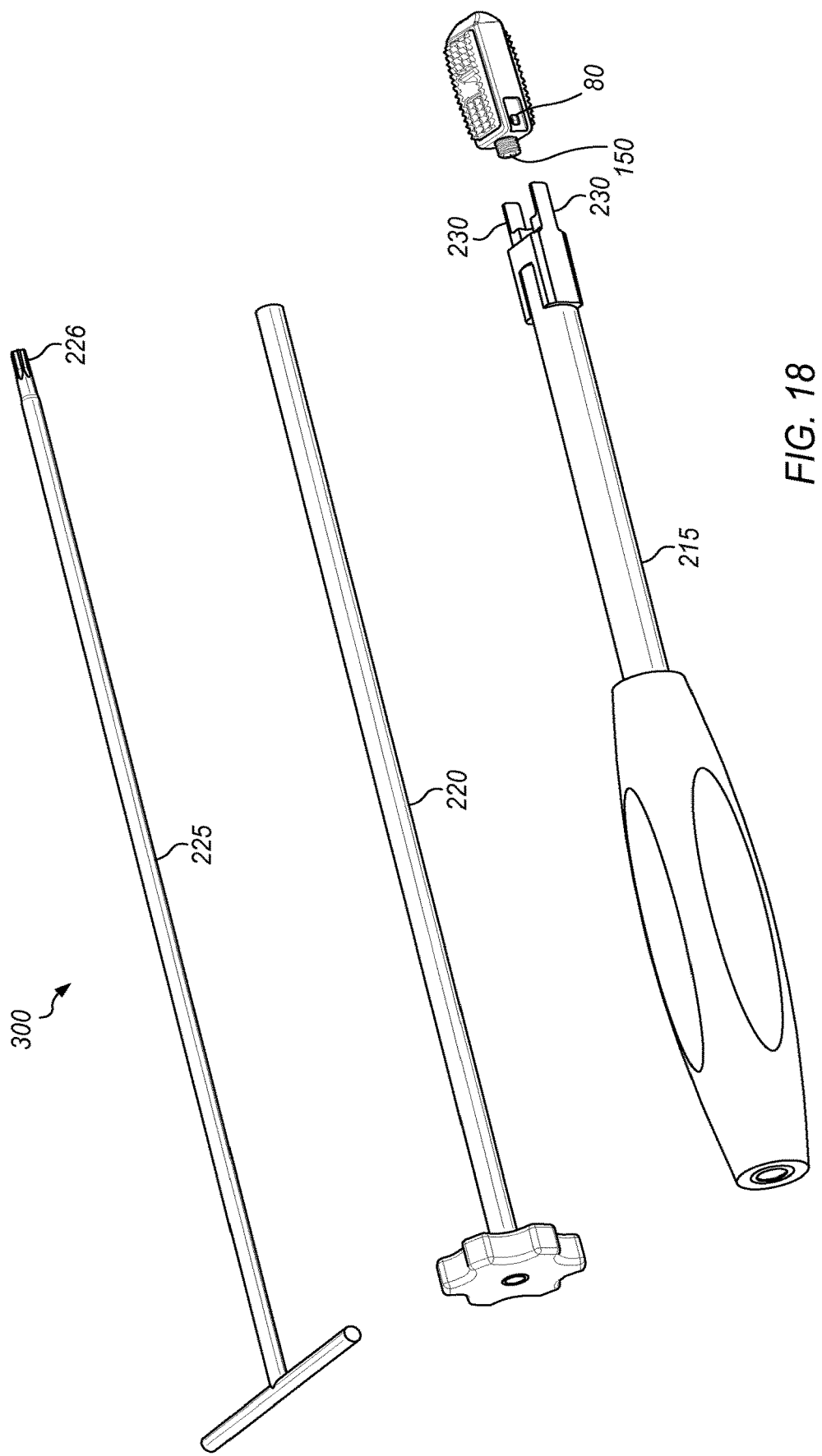
FIG. 18 depicts a schematic view showing insertion instruments for use with an expandable fusion device.

In some embodiments, an implant system may include an implant insertion device 300. FIG. 18 shows a handle 215, a holder 220 and an engaging member 225 which may be used to manipulate and deploy intervertebral implant 5. More particularly, handle 215 includes two extensions 230 for positioning in seats 80 (e.g., as depicted in FIGS. 3-6) of intervertebral implant 5. Holder 220 may be positionable in handle 215 and threadingly engages the distal end of expansion mechanism 45, whereby to releasably secure intervertebral implant 5 to handle 215. Engaging member 225 may be positionable in holder 220 and into bore 150 in expansion mechanism 45, whereby to permit the user to turn expansion mechanism 45 and hence adjust the height of the intervertebral implant 5. Engaging member 225 may include engaging head 226 which engages bore 150. Engaging head 226 may include a complementary shape to bore 150 such that as the head turns the expansion member 45 turns.

Figure 24:
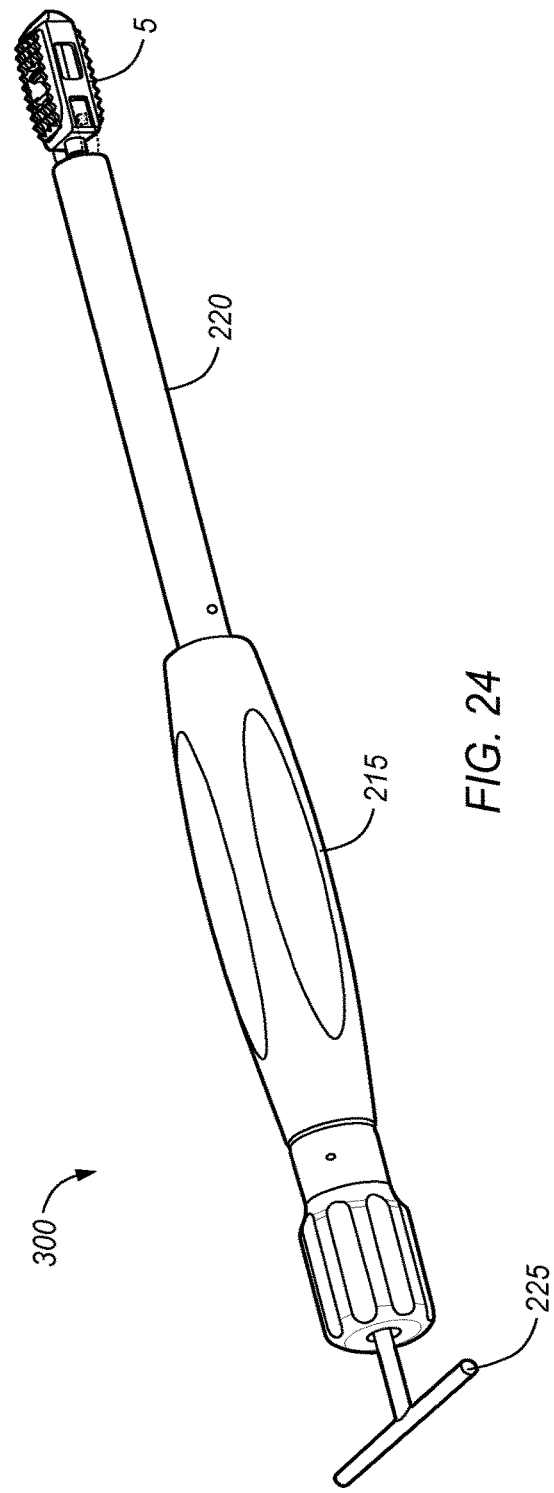
FIG. 24 depicts a schematic view showing insertion instruments for use with an expandable fusion device.
Figure 25:
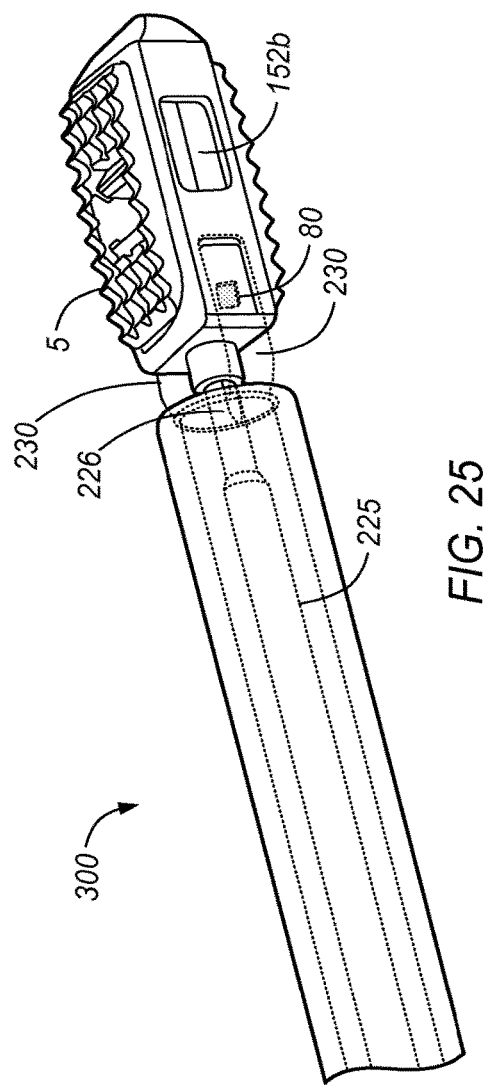
FIG. 25 depicts a schematic view showing a distal end of an insertion instrument for use with an expandable fusion device.
Figure 26:
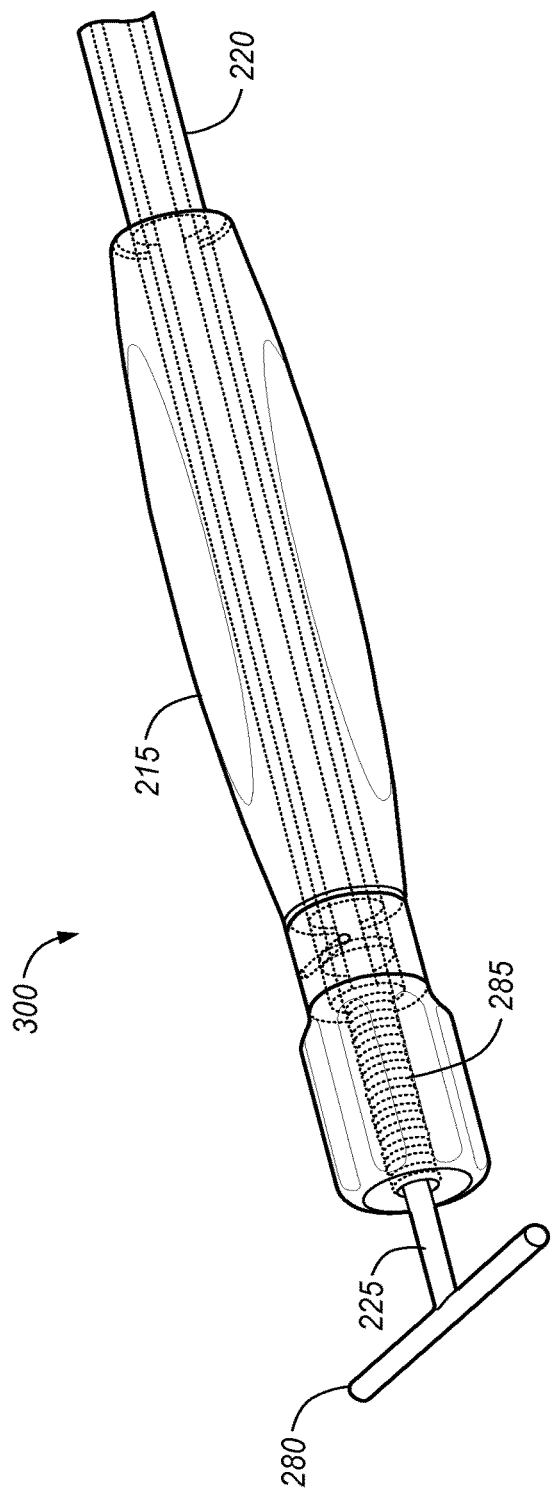
FIG. 26 depicts a schematic view showing a proximal end of an insertion instrument for use with an expandable fusion device.

In some embodiments, an implant system may include an implant insertion device 300. FIGS. 24-26 depict a schematic view showing insertion instruments 300 for use with an expandable fusion device. FIGS. 24-26 depict a handle 215, a holder 220 and an engaging member 225 which may be used to manipulate and deploy intervertebral implant 5. More particularly, handle 215 includes two extensions 230 for positioning in seats 80 (e.g., as depicted in FIGS. 24-25) of intervertebral implant 5. Engaging member 225 may be positionable in holder 220 and into bore 150 in expansion mechanism 45, whereby to permit the user to turn expansion mechanism 45 and hence adjust the height of the intervertebral implant 5. Engaging member 225 may include engaging head 226 which engages bore 150. Engaging head 226 may include a complementary shape to bore 150 such that as the head turns the expansion member 45 turns. In some embodiments, the insertion instrument 300 may include a grip 280 coupled to engaging member 225. In some embodiments, engaging member 225 may include a threaded proximal portion 285. The threaded portion 285 may function to assist in controlling longitudinal movement of the engaging member and therefore expansion of the implant.

Figure 27:
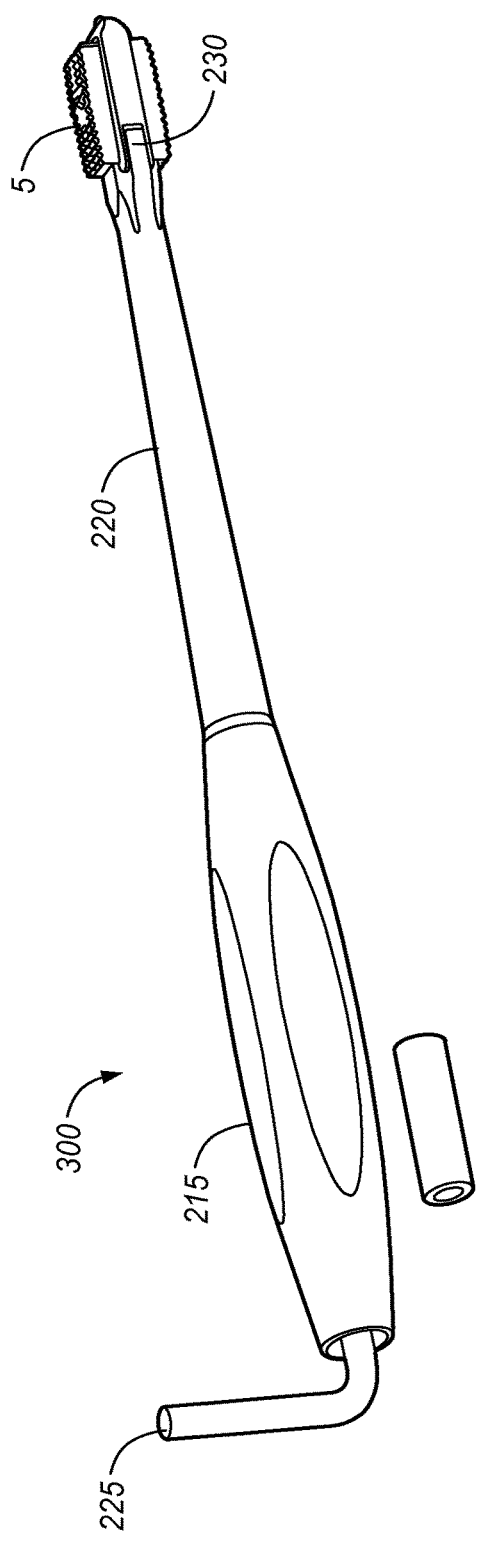
FIG. 27 depicts a schematic view of a disposable expandable fusion implant insertion device.
Figure 28:
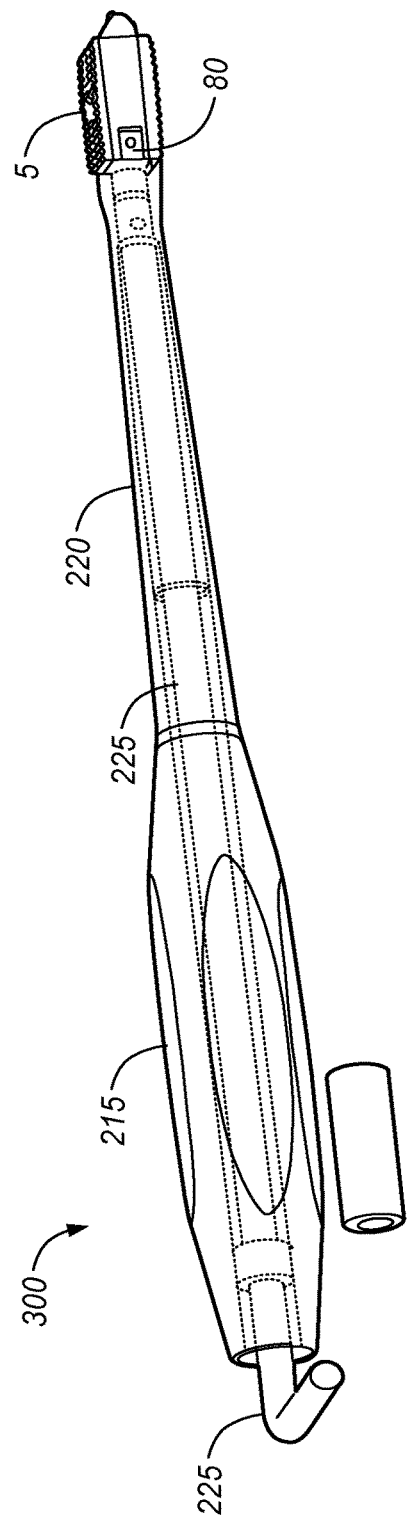
FIG. 28 depicts a schematic transparent view of a disposable expandable fusion implant insertion device.

In some embodiments, an insertion device may be disposable. FIGS. 27-28 depict a schematic view of a disposable expandable fusion implant insertion device 300. A disposable insertion device may be packaged with an implant. The insertion device may allow bone graft to be packed after insertion. The "disposable" option may allow the holder to act as an internal funnel which would make cleaning difficult, but a "durable version" remains an option. In some embodiments, engaging member 225 may be used to pack biological material into the implant through holder 220. In some embodiments, a separate packing instrument (not depicted) may be used to insert biological material.

FIGS. 32-36 depict a schematic view showing insertion instruments 300 for use with an expandable fusion device. FIGS. 32-36 depict a handle 215, a holder 220 and an engaging member 225 which may be used to manipulate and deploy intervertebral implant 5. More particularly, handle 215 includes two extensions 230 for positioning in seats 80 (e.g., as depicted in FIGS. 24-25) of intervertebral implant 5. In some embodiments, the extensions may be spring loaded (e.g., using springs, forming at least a portion of the extensions from an at least slightly flexible material, etc.) such that they are biased to be positioned such that they apply pressure to the seats of the implant during use. In some embodiments, a mechanism may be employed to engage/release the extensions from the implant.

The insertion instrument may include at least two holders 220 which couple to opposing sides (e.g., the inferior and superior surfaces of the implant) of the implant during use. In some embodiments, the holders may be spring loaded (e.g., using springs, forming at least a portion of the holders from an at least slightly flexible material, etc.) such that they are biased to be positioned such that they apply pressure to the surfaces of the implant during use. In some embodiments, a mechanism may be employed to engage/release the holders from the implant. The holders may include a curved edge or lip which curve towards one another. The curved edge may engage an appropriately shaped portion of the proximal end of the implant.

Engaging member 225 may be positionable in handle 215 and into bore 150 in expansion mechanism 45, whereby to permit the user to turn expansion mechanism 45 and hence adjust the height of the intervertebral implant 5. Engaging member 225 may include engaging head 226 which engages bore 150. Engaging head 226 may include a complementary shape to bore 150 such that as the head turns the expansion member 45 turns. In some embodiments, the insertion instrument 300 may include a grip 280 coupled to engaging member 225.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for increasing the spacing between two adjacent vertebral bodies, the method comprising:

removing at least a portion of a disc between two vertebrae of the human spine to create a space between the two vertebrae;

positioning an intervertebral implant in the space between the two vertebrae, wherein the intervertebral implant comprises:

a cage comprising a first end portion, a second end portion, a longitudinal axis extending between the first end portion and the second end portion, an upper portion and a lower portion;

an upper body movably mounted to the cage, the upper body comprising an inferior surface and a superior surface;

a lower body movably mounted to the cage, the lower body comprising a superior surface and an inferior surface;

a first expansion member comprising at least a first inclined portion, wherein at least the first inclined portion is oriented towards the first end portion of the cage;

a second expansion member comprising at least a second inclined portion, wherein at least the second inclined portion is oriented towards the second end portion of the cage; and an expansion mechanism movably mounted to the cage, wherein the expansion mechanism comprises a threaded portion for threadingly engaging a threaded portion of the first expansion member, and further wherein the second expansion member is non-threadingly coupled to the expansion mechanism, such that when the expansion mechanism is rotated, the expansion mechanism moves relative to the cage, the first expansion member is moved relative to the cage and relative to the expansion mechanism, and the second expansion member is moved relative to the cage in the opposing direction, so as to increase a separation distance between the upper body and the lower body; and rotating the expansion mechanism so as to move the first and second expansion members in opposing directions so as to increase a separation distance between the upper body and the lower body.

2. The method of claim 1; further comprising engaging a first vertebra of the human spine using the superior surface of the upper body.

3. The method of claim 2, wherein the superior surface of the upper body comprises teeth for engaging the first vertebra.

4. The method of claim 1, further comprising engaging a second vertebra of the human spine using the inferior surface of the lower body.

5. The method of claim 4, wherein the inferior surface of the lower body comprises teeth for engaging the second vertebra.

6. The method of claim 1, wherein, when the expansion mechanism is rotated, the first inclined portion of the first expansion member moves towards the first end portion of the cage and the second inclined portion of the second expansion member moves towards the second end portion of the cage.

7. The method of claim 1, wherein, when the expansion mechanism is rotated, one of the first expansion member and the second expansion member moves a further distance relative to the cage than the other of the first expansion member and the second expansion member.

8. The method of claim 1, wherein, before rotation of the expansion mechanism, the superior surface of the upper body and the inferior surface of the lower body are parallel to the longitudinal axis of the cage.

9. The method of claim 1, wherein, before rotation of the expansion mechanism, the superior surface of the upper body and the inferior surface of the lower body are both inclined relative to the longitudinal axis of the cage.

10. The method of claim 1, wherein, after rotation of the expansion mechanism, the superior surface of the upper body and the inferior surface of the lower body are parallel to the longitudinal axis of the cage.

11. The method of claim 1, wherein; after rotation of the expansion mechanism, the superior surface of the upper body and the inferior surface of the lower body are both inclined relative to the longitudinal axis of the cage.

12. The method of claim 1, wherein the first inclined portion of the first expansion member comprises a flat surface.

13. The method of claim 1, wherein the second inclined portion of the second expansion member comprises a flat surface.

14. The method of claim 1, wherein the first inclined portion of the first expansion member comprises a curved surface.

15. The method of claim 1, wherein the second inclined portion of the second expansion member comprises a curved surface.

16. The method of claim 1 wherein the first inclined portion of the first expansion member comprises a first geometry, the second inclined portion of the second expansion member comprises a second geometry, and further wherein the first geometry is different from the second geometry.

17. The method of claim 1, wherein the cage forms a perimeter for the intervertebral implant, and further wherein at least portions of the upper body, the lower body, the first expansion member, the second expansion member, and the expansion mechanism are positioned within the perimeter.

18. The method of claim 17, wherein the cage comprises a curved shape such that a first portion of the perimeter is substantially convex and a second portion of the perimeter is substantially concave, wherein the second portion is substantially opposite the first portion.

19. The method of claim 17, wherein the cage comprises one or more openings along the perimeter to allow graft material to be positioned during use.

20. The method of claim 1, wherein at least one of the upper body and the lower body comprises an opening within which graft material is positionable during use.

21. The method of claim 1, wherein the upper body and the lower body define an opening therebetween, and further wherein this opening increases in size as the first and second inclined portions of the first and second expansion members, respectively, are moved.

* * * * *